US010561658B2

(12) United States Patent
Radtke et al.

(10) Patent No.: US 10,561,658 B2
(45) Date of Patent: Feb. 18, 2020

(54) THIENO- AND PYRROLOPYRIMIDINE ANALOGUES AS ANTICANCER AGENTS AND METHODS OF USE THEREOF

(71) Applicant: UNIVERSITY OF MARYLAND, BALTIMORE COUNTY, Baltimore, MD (US)

(72) Inventors: Katherine L. Radtke, Silver Spring, MD (US); Kartik Temburnikar, Tempe, AZ (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 0 days.

(21) Appl. No.: 15/893,779

(22) Filed: Feb. 12, 2018

(65) Prior Publication Data

US 2018/0161330 A1  Jun. 14, 2018

Related U.S. Application Data

(63) Continuation of application No. 15/249,980, filed on Aug. 29, 2016, now Pat. No. 9,895,374, which is a continuation of application No. 14/634,940, filed on Mar. 2, 2015, now Pat. No. 9,434,742.

(51) Int. Cl.
*A61K 31/519* (2006.01)
*C07D 495/04* (2006.01)
*C07D 487/04* (2006.01)

(52) U.S. Cl.
CPC .......... *A61K 31/519* (2013.01); *C07D 487/04* (2013.01); *C07D 495/04* (2013.01)

(58) Field of Classification Search
CPC ... A61K 31/519; C07D 487/04; C07D 495/04
USPC .............. 544/278, 280; 514/260.1
See application file for complete search history.

(56) References Cited

U.S. PATENT DOCUMENTS 9,434,742 B1  9/2016  Radtke

FOREIGN PATENT DOCUMENTS

| DE | 2137341 | * | 10/1973 | ............. | C07D 51/46 |
| GB | 1057612 | * | 2/1967 | ............. | C07D 99/06 |
| GB | 1391161 A | * | 5/1975 | ........... | C07D 495/02 |
| WO | WO2009062258 | | 5/2009 | | |

OTHER PUBLICATIONS

Imai, Kinichi, Chemical & Pharmaceutical Bulletin (1964), 12(9), 1030-42.*
Bambuch, et. al., Tetrahedron (2007), 63(7), 1589-1601.*
Alcindor, T. et al. Oxaliplatin: a review in the era of molecularly targeted therapy. *Curr Oncol.* 2011 18(1): p. 18-25.
Amarnath, V.M. et al. Survey of methods for the preparation of pyrrolopyrimidines. *Synthesis* 1974: p. 83-859.
Bastos, D.A. et al., Combination therapy in high-risk stage II or stage III colon cancer: current practice and future prospects. *Ther Adv Med Oncol.* 2010, 2(4): p. 261-72.
Braun, M.S. et al. Balancing the efficacy and toxicity of chemotherapy in colorectal cancer. *Ther Adv Med Oncol.* 2011, 3(1): p. 43-52.
Chandra, S. et al. Targeted therapies for metastatic melanoma, *Dermatologic clinics* 2012, 30, 517-524.
Crespo, M.I., et al., Design, synthesis, and biological activities of new thieno[3,2-d]pyrimidines as selective type 4 phosphodiesterase inhibitors. *J Med Chem*, 1998. 41(21): p. 4021-35.
Das Thakur, M. et al. Modelling vemurafenib resistance in melanoma reveals a strategy to forestall drug resistance, *Nature* 2013, 494(7436), 251-255.
Evans, G. B. et al. Addition of Lithiated 9-Deazapurine Derivatives to a Carbhydrate Cyclic Imine: Convergent Synthesis of the Aza-C-nucleoside Immunocillins. *J Org. Chem.* 2001, 66, 5723-5730.
Flaherty, K.T. Chemotherapy and targeted therapy combinations in advanced melanoma. *Clin Cancer Res*, 2006. 12(7 Pt 2): p. 2366s-2370s.
Foley, G. E.; Lazarus, H.; Farber, S.; Uzman, B. G.; Boone, B. A.; McCarthy, R. E. *Cancer* 1965, 18, 522-529.
Golub, A.G. et al., Synthesis and biological evaluation of substituted (thieno[2,3-d]pyrimidin-4-ylthio)carboxylic acids as inhibitors of human protein kinase CK2. *Eur J Med Chem.* 2011, 46(3): p. 870-6.
Guimaraes, C. R. W. et al. Thermodynamic Analysis of mRNA Cap Binding by the Human Initiation Factor eIF4E via Free Energy Perturbations, *J. Am. Chem. Soc.* 2009, 131, 18139-18146.
Haggar, F.A. et al. Colorectal cancer epidemiology: incidence, mortality, survival, and risk factors. *Clin Colon Rectal Surg*, 2009. 22(4): p. 191-7.
Hoelder, S. et al. Discovery of small molecule cancer drugs: successes, challenges and opportunities. *Mol Oncol.* 2012 6(2): p. 155-76.
Ife, R.J. et al. Reversible inhibitors of the gastric (H+/K+)-ATPase. 5. Substituted 2,4-diaminoquinazolines and thienopyrimidines. *J Med Chem*, 1995. 38(14): p. 2763-73.
Imai, Kin-ichi, Studies on Nucleic Acid Antagonists, *Chemical and Pharmaceutical Bulletin* 1964, 12(9), 1030-42.
Jang, S. et al. Which drug, and when, for patients with BRAF-mutant melanoma?, *The Lancet Oncology* 2013, 14, e60-e69.
Jordan, E. J. et al. Vemurafenib for the treatment of melanoma, *Expert opinion on pharmacotherapy* 2012, 13, 2533-2543.
Lim, M.K. Synthesis of the pyrrolo[3,2-d]pyrimidine C-nucleoside isostere of inosine. *Tet. Lett*, 1980(21): p. 1013-1016.
Lim, M.K. et al. Synthesis of "9-deazaadenosine"; a new cytotoxic C-nucleoside isostere of adenosine. *Tet. Lett.*, 1981(22): p. 25-28.
Lim, M.R. et al. Synthesis of "9-deazaguanosine" and other new pyrrolo[3,2-d]pyrimidine C-nucleosides. *J. Org. Chem.*, 1983(48): p. 780-788.

(Continued)

*Primary Examiner* — Jeffrey H Murray
(74) *Attorney, Agent, or Firm* — Tristan A. Fuierer; Marianne Fuierer; Olive Law Group, PLLC

(57) ABSTRACT

The present invention provides for the design and synthesis of halogenated thieno- and pyrrolopyrimidine compounds that exhibit cancer proliferation inhibitory activity and the use thereof for cancer treatment.

7 Claims, 14 Drawing Sheets

(56) References Cited

OTHER PUBLICATIONS

Maio, M. et al. Update on the role of ipilimumab in melanoma and first data on new combination therapies, *Current opinion in oncology* 2013, 25, 166-172.

Mollard, A. et al. Design, Synthesis, and Biological Evaluation of a Series of Novel AXL Kinase Inhibitors. *ACS Med. Chem. Lett.* 2011, 2, 907-912.

Nandan, M.O. et al. An Update on the Biology of RAS/RAF Mutations in Colorectal Cancer. *Curr Colorectal Cancer Rep.* 2011, 7(2): p. 113-120.

Pasetto, L.M., et al., FOLFOX versus FOLFIRI: a comparison of regimens in the treatment of colorectal cancer metastases. *Anticancer Res*, 2005. 25(1B): p. 563-76.

Pedeboscq, S., et al. Synthesis and evaluation of apoptosis induction of thienopyrimidine compounds on KRAS and BRAF mutated colorectal cancer cell lines. *Bioorg Med Chem.* 2012, 20(22): p. 6724-31.

Ren, W.L. et al. Synthetic studies of the thieno[3,2-d]pyrimidine C-nucleoside isostere of inosine. *J. Org. Chem.*, 1982(47): p. 4633-4637.

Ren, W.R. et al. Convenient synthesis of substituted 3-aminothiophene-2-carbonitriles from α-acetylenic nitriles and their conversion to thieno[3,2-d]pyrimidines. *J. Heterocycl. Chem*, 1986(23): p. 1757-1763.

Russell, R.K., et al. Thiophene systems. 9. Thienopyrimidinedione derivatives as potential antihypertensive agents. *J Med Chem*, 1988. 31(9): p. 1786-93.

Safina, B.S. et al. Discovery of novel PI3-kinase delta specific inhibitors for the treatment of rheumatoid arthritis: taming CYP3A4 time-dependent inhibition. *J Med Chem.* 2012, 55(12): p. 5887-900.

Scherer, W. F. et al. Studies of the Propogation in Vitro of Poliomyelitis Viruses. IV. Viral Multiplication ina Stable Strain of Human Malignant Epithelial Cells (Strain Hela) Derived from an Epidermoid Carcinoma of the Cervix. *J. Exp. Med.* 1953, 97, 695-710.

Seley, K.L., et al. Synthesis and antitumor activity of thieno-separated tricyclic purines. *J Med Chem*, 2000. 43(25): p. 4877-83.

Showalter, H.D. et al., Tyrosine kinase inhibitors. 16. 6,5,6-tricyclic benzothieno[3,2-d]pyrimidines and pyrimido[5,4-b-] and -[4,5-b]indoles as potent inhibitors of the epidermal growth factor receptor tyrosine kinase. *J Med Chem*, 1999. 42(26): p. 5464-74.

Sutherlin, D.P. et al. Discovery of a potent, selective, and orally available class I phosphatidylinositol 3-kinase (PI3K)/mammalian target of rapamycin (mTOR) kinase inhibitor (GDC-0980) for the treatment of cancer. *J Med Chem.* 2011, 54(21): p. 7579-87.

Sutherlin, D.P. et al. Discovery of (thienopyrimidin-2-yl)aminopyrimidines as potent, selective, and orally available pan-PI3-kinase and dual pan-PI3-kinase/mTOR inhibitors for the treatment of cancer. *J Med Chem.* 2010, 53(3): p. 1086-97.

Tan, C. et al. KRAS mutation testing in metastatic colorectal cancer. *World J Gastroenterol.* 2012, 18(37): p. 5171-80.

Temburnikar, K. et al. Synthesis of 2'-deoxy-9-deaza nucleosides using Heck methodology. *J Org Chem.* 2013, 78(14): p. 7305-11.

Temburnikar, K. et al. Modified synthesis of 3'-O-TBDPS-protected furanoid glycal. *Nucleosides Nucleotides Nucleic Acids.* 2012, 31(4): p. 319-27.

Temburnikar, K. W. et al. Antiproliferate activities of halogenated thieno[3,2-d]pyrimidines. *Bioorg. Med. Chem.* 2014, 22, 2113-2122.

Zeng, S. et al., Discovery of potent dipeptidyl peptidase IV inhibitors through pharmacophore hybridization and hit-to-lead optimization. *Bioorg Med Chem.* 2013, 21(7): p. 1749-55.

Zong, W.X. et al., Alkylating DNA damage stimulates a regulated form of necrotic cell death. *Genes Dev*, 2004. 18(11): p. 1272-82.

\* cited by examiner

| CANCER | CELL LINE | GROWTH PERCENT | | |
|---|---|---|---|---|
| | | 1 | 2 | 19 |
| Melanoma | LOX IMVI | 21.22 | 4.91 | 15.11 |
| | MDA-MB-435 | 37.40 | 80.55 | -34.15 |
| Breast | T47D | 60.08 | 2.59 | 74.85 |
| | BT549 | 97.03 | 80.35 | -3.66 |
| CNS | SF-268 | 72.98 | 91.48 | 23.09 |
| | SNB-75 | 95.00 | 99.64 | 55.13 |
| Non-small cell lung | NIC-H226 | 99.82 | 105.36 | 57.41 |
| | NCI-H23 | 94.85 | 103.40 | 87.27 |
| GI50 IN 5-DOSE SCREEN | | 4.57 E-07M | 2.09E-07M | ND |

Figure 4

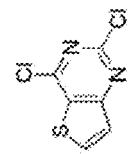

NCI 60 cell line (5-dose) screen

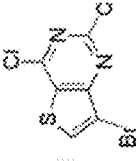

| Panel/Cell Line | GI50 a | TGI b | LC50 c | Panel/Cell Line | GI50 a | TGI b | LC50 c |
|---|---|---|---|---|---|---|---|
| Leukemia | | | | | | | |
| CCRF-CEM | 3.47E-06 | 1.49E-05 | >1.00E-4 | CCRF-CEM | 1.33E-06 | 4.03E-06 | >1.00E-4 |
| MOLT-4 | 3.55E-06 | 2.06E-05 | >1.00E-4 | MOLT-4 | 2.18E-06 | 4.55E-06 | 9.49E-06 |
| RPMI-8226 | 4.06E-06 | 1.83E-05 | >1.00E-4 | RPMI-8226 | 2.79E-06 | - | >1.00E-4 |
| SR | 2.17E-06 | 1.01E-05 | 9.60E-05 | SR | 2.86E-07 | 1.12E-06 | >1.00E-4 |
| Non-Small Cell Lung Cancer | | | | | | | |
| HOP-62 | 7.18E-06 | 3.48E-05 | >1.00E-4 | HOP-92 | 1.89E-06 | 3.61E-06 | 7.70E-06 |
| NCI-H460 | 3.04E-06 | 8.46E-06 | 3.71E-05 | NCI-H460 | 3.01E-06 | 7.73E-06 | >1.00E-4 |
| NCI-H522 | 4.67E-07 | 1.81E-06 | 8.46E-06 | NCI-H522 | 2.09E-07 | 4.33E-07 | 8.97E-07 |
| Colon Cancer | | | | | | | |
| HT29 | 3.75E-06 | 1.41E-05 | >1.00E-4 | HT29 | 2.00E-06 | 3.85E-06 | 7.43E-06 |
| Ovarian Cancer | | | | | | | |
| OVCAR-8 | 3.65E-06 | 1.94E-05 | >1.00E-4 | OVCAR-8 | 2.02E-06 | 4.46E-06 | |
| ADR-RES | 3.96E-06 | 1.71E-05 | >1.00E-4 | ADR-RES | 2.34E-06 | 5.17E-06 | >1.00E-4 |
| Breast Cancer | | | | | | | |
| HS 578T | 6.53E-06 | 4.34E-05 | >1.00E-4 | HS 578T | 4.55E-06 | 5.21E-05 | >1.00E-4 |
| T-47D | 5.66E-06 | 2.39E-05 | >1.00E-4 | T-47D | 2.15E-06 | 4.74E-06 | >1.00E-4 | a. concentration to inhibit cell growth by 50%, b. concentration required for total growth inhibition, c. 50% lethal concentration

Figure 13

THIENO- AND PYRROLOPYRIMIDINE ANALOGUES AS ANTICANCER AGENTS AND METHODS OF USE THEREOF

CROSS REFERENCE TO RELATED APPLICATIONS

The present invention is a continuation application and claims priority to U.S. patent application Ser. No. 15/249,980, filed on Aug. 29, 2016, now U.S. Pat. No. 9,895,374, which in turn is a continuation of and claims priority to U.S. patent application Ser. No. 14/634,940, filed on Mar. 2, 2015, now U.S. Pat. No. 9,434,742, the contents of which are incorporated by reference herein for all purposes.

FIELD OF INVENTION

The present invention provides for the design and synthesis of halogenated thieno- and pyrrolopyrimidine compounds that exhibit cancer proliferation inhibitory activity and the use thereof for cancer treatment.

BACKGROUND OF THE INVENTION

The advent of molecularly targeted anticancer therapies has energized the cancer field and given new hope to cancer patients. Discovery of intracellular pathways that can lead to tumor growth suppression and the development of monoclonal antibodies that specifically target cancer pathways are being developed and tested in human clinical trials. The dawn of such targeted anticancer therapies could cause a certain lack of interest in the development of novel conventional cytotoxic small molecule drugs. However, molecularly targeted therapies have not shown improved curative properties when administered as monotherapy [1]. As a result, most molecularly targeted agents today are used in combination with cytotoxic compounds.

In contrast to the tumor-static activities of many targeted agents, cytotoxic agents have the ability to directly kill cancer cells through their inhibition of critical cell growth pathways and exert a broader range of activity as compared to targeted therapies that are inherently narrow. For these reasons, there is hope in combining molecular targeted anticancer therapies with conventional cytotoxic chemotherapy [2, 3]. Indeed, current standard of care treatments are based on sequential therapies by combining multiple drugs with the intent of overcoming drug-resistance, which is typical of many tumors and a major issue in fighting cancer. In the age of targeted therapies and therapeutic monoclonal antibodies, it is noteworthy that extensive resources and scores of clinical trials are still being devoted to the identification and evaluation of small molecules chemotherapy agents, thus reiterating the need for improved chemotherapy drugs. This is partly due to an extremely large untapped reservoir of potential therapeutic compounds which tackle several biological aspects of a highly proliferating living cell and also to the growing understanding of the life cycle of cancer cells and onset of drug-resistance. Overall, there is still a need to develop more effective cytotoxic drugs. These new chemotherapy drugs need to show an increased potency, low systemic toxicity, better bioavailability and that can be used in combination with current approved drugs.

Among cancers, the high incidence and mortality of colorectal cancer is a major health issues worldwide [4, 5]. While the ability to treat patients with colorectal cancer has improved in the past 15 years, thanks to optimized surgery techniques, better radiotherapy and novel chemotherapy drugs, treatments are still not ideal. Major toxicities (grade 3 or 4) are still a problem with standard-of-care chemotherapy drugs. 5FU, irinotecan, leucovorin, oxaliplatin, either alone or in the FOLFOX or FOLFIRI regimens, result in severe side effects that can also developed into neuronal toxicity [6, 7]. Targeted therapies displayed overall less side effects events when administered alone, however, combinations with chemotherapy drugs is typically more effective in colorectal patients, especially when RAS/RAF mutations are present. For the latter, the identification of KRAS and BRAF mutations in colorectal cancer patients has become a crucial diagnostic factor for designing effective therapy regimens that could treat also metastatic colorectal cancers [8, 9].

Additionally, melanoma cancer rates have risen steadily for the last 30 years. Nonetheless, the median survival is <1 year and the 5 year survival rate is 10%. [30, 31]. Two targeted therapies were approved in 2011, ipilimumab (a monoclonal antibody) and vemurafenib (a BRAF kinase inhibitor), that exhibit robust anti-tumor activity, but patients relapse with lethal drug resistant disease within 5-7 months. [32-35] The biological response modifier adesleukin (recombinant interleukin-2) has a 50-60% response rate, but can produce life-threatening toxicities. The response rate for temozolomide, a DNA modifying agent, is <20%.

Breast cancer is a major cause of cancer-related death in women preceded only by lung cancer.[43] The expression levels of estrogen receptors (ER) and progesterone receptors (PR) as well as the amplification status of the HER-2/Neu gene help direct diagnosis and treatment of breast cancer. For tumors that express one or more of these biomarkers, targeted therapies have significantly improved patient outcomes. However, breast cancers lacking the aforementioned biomarkers, termed triple negative breast cancer (TNBC), present severe challenges for patient survival since biomarker-targeted therapies are ineffective.

As discussed above, current therapies are not always effective, and as such, there is a need for improved drugs with higher activity for treating cancers with minimum side effects that can be used in alone, combinational and/or sequential treatments.

SUMMARY OF THE INVENTION

The present invention provides for nucleobase analogues, that being, halogenated thieno- and pyrrolopyrimidine compounds with the ability to induce apoptosis and inhibit growth of cancer cells at low nM concentrations. The activity of these compounds is effective against numerous types of cancers including colon, renal, breast and melanoma.

The present invention also relates to the induction of cancer cell apoptosis with halogenated pyrrolopyrimidines and thienopyrimidines for reducing tumor burden without inhibiting kinases. As such, this lessens their potential for mitochondrial toxicity by inhibition of pol gamma or other human polymerases.

In one aspect, the present invention provides for a nucleobase analogue compound of formula (I) or a pharmaceutically acceptable salt, hydrate or solvate thereof:

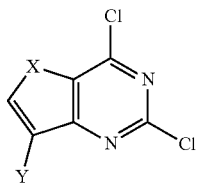

(I)

wherein X is S or NH and Y is H, Br or I.

In another aspect, the present invention provides for a method of inducing apoptosis and/or inhibiting the growth of cancer cells, the method comprising administering a therapeutically effective amount of a halogenated pyrrolopyrimidine and/or thienopyrimidine molecule have the following formula:

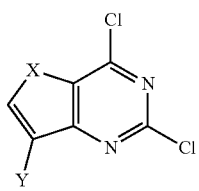

(I)

wherein X is S or NH and Y is H, Br or I.

In yet another aspect, the present invention provides for a nucleobase analogue compound of formula (II) or a pharmaceutically acceptable salt, hydrate or solvate thereof:

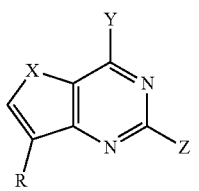

(II)

wherein X is S, I or NH;
R is H, Br, NH or I;
Y is I, Cl, OCH$_3$, O-benzyl, F, NH$_2$ or C$_2$H$_3$N$_3$; and
Z is Cl, O-benzyl, F or OCH$_3$.

In a further aspect, the present invention provides for the use of a compound of formula (I), formula (II) or a pharmaceutically acceptable salt, hydrate, prodrug or solvate thereof, in the manufacture of a medicament for the treatment of cancer.

In another aspect, the present invention provides for a pharmaceutical composition comprising a compound of formula (I) or formula (II), or a pharmaceutically acceptable salt, hydrate or solvate thereof, and a pharmaceutically acceptable carrier.

In yet another aspect, the present invention provides for contacting a cell in an animal, such as a human cell, with at least one of the nucleobase analogues provided herein.

Other aspects, features and embodiments of the invention will be more fully apparent from the ensuing disclosure and appended claims.

BRIEF DESCRIPTION OF THE FIGURES

FIG. 4 shows the results of anti-cancer activity of lead compounds and the growth percent of representative cancer cell line from the NCI60 cell line (1 dose).

FIG. 5 (B) shows apoptosis of compound 2 (iii) and compound 19 (iv).

FIG. 13 shows the results of anti-cancer activity of lead compounds 1 and 2 and the growth percent of representative cancer cell line from the NCI60 cell line (5 dose).

DETAILED DESCRIPTION OF THE INVENTION

Figure 1A:
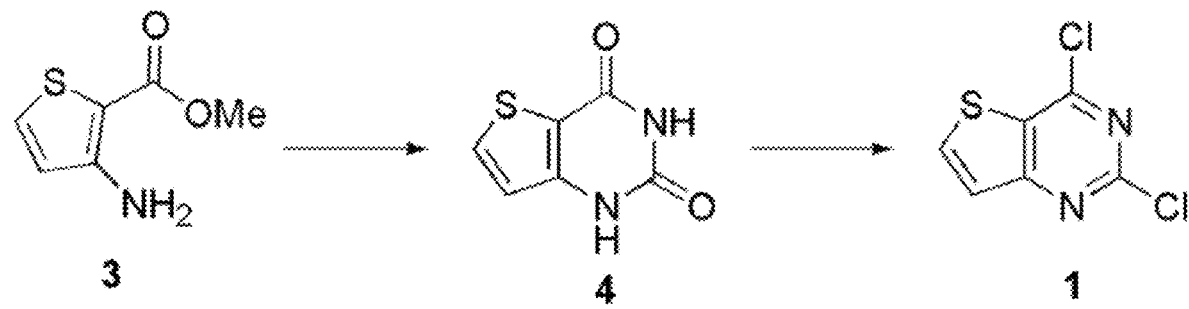
FIG. 1 (A) is a scheme for synthesis of 2,4-Dichlorothieno[3,2-d]pyrimidine (1), FIG. 1 (B) scheme for synthesis of Bromo-2,4-dichlorothieno[3,2-d]pyrimidine (2).

The thieno[3,2-d]pyrimidine compounds are known because of their close resemblance to the purines, arguably the most biologically significant class of bicyclic heterocyclic compounds [10-15]. Indeed, thienopyrimidine derivatives have been extensively studies by several independent groups and several molecules have been identified with antiviral, antimicrobial or kinase inhibition activities. In addition, thienopyrimidine scaffolds carrying an aromatic ring substituent possess enhanced anti-tumor activity, which was proved by testing them against colorectal cancer cell lines. However, such cancer proliferation inhibitory activity was fairly modest, with an $IC_{50}$ in the high uM range [16-25].

The present inventors have has worked on the generation of thiophene "extended" pyrimidine nucleosides [26, 27] but such nucleosides showed only modest results for anti-cancer activities [28].

In the present invention it has been found that halogenated pyrrolopyrimidines and thienopyrimidines compounds are pharmacologically useful scaffolds that manifest anti-tumor activity against cancer by at least inducing apoptosis. Importantly, it has been found that a halogen at the C4 and/or C7 exhibits increase potency. In preferred embodiments, Y at C4 is chlorine or O-Benzyl, R at C7 is I and X is S or NH.

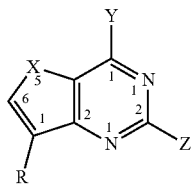

Definitions

The term "treat" or "treatment" as used herein refers to both therapeutic treatment and prophylactic or preventative measures, wherein the compound is to slow down (lessen) an undesired pathological change or disorder, such as the development or spread of cancer. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, "treatment" can include a qualitative or quantitative reduction (e.g., by at least 10%, 20%, 30%, 40%, 50%, 60%, 70%, 80%, 90%, 95%, or more) in the tumor or metastases size or reduce or prevent metastatic growth. "Treatment" can also mean prolonging survival as compared to expected survival if not receiving treatment.

The phrase "therapeutically effective amount" as used herein refers to an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may be reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can be measured, for example, by assessing the time to disease progression (TTP) and/or determining the response rate (RR).

The terms "cancer" or "cancerous" as used herein refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatome, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "salt" as used herein includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

The term 'solvate' as used herein refers to a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned may exist in one or more stereoisomeric form because of the presence of asymmetric atoms or rotational restrictions and can exist as a number of stereoisomers with R or S stereochemistry at each chiral centre or as atropisomers with R or S stereochemistry at each chiral axis. The invention includes all such enantiomers and diastereoisomers and mixtures thereof.

While it may be possible for compounds of the present invention to be administered as the raw chemical, it is preferable to present them as a pharmaceutical composition. According to a further aspect, the present invention provides a pharmaceutical composition comprising a compound or a mixture of compounds of Formula (I) and/or Formula (II) or a pharmaceutically acceptable salt, solvate or hydrate thereof, together with one or more pharmaceutical carrier, excipient or additive and optionally one or more other therapeutic ingredients. The carrier(s) must be "acceptable" in the sense of being compatible with the other ingredients of the formulation and not deleterious to the recipient thereof. The term "pharmaceutically acceptable carrier" includes vehicles and diluents.

To prepare the pharmaceutical compositions, a therapeutically effective amount of one or more of the halogenated pyrrolopyrimidines and thienopyrimidines according to the present invention may be admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

In one embodiment, the compositions are prepared with carriers that will protect the active compound(s) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The pharmaceutically acceptable carrier may take a wide variety of forms, depending on the route desired for administration, for example, oral or parenteral (including intravenous). Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

In an embodiment, the composition of the present invention enables sustained, continuous delivery of a compound of Formula (I) or Formula (II) a pharmaceutically acceptable salt, solvate or hydrate thereof, to tissues adjacent to or distant from an administration site. The biologically-active agent is capable of providing a local or systemic biological, physiological or therapeutic effect. For example, a compound of Formula (I) or Formula (II) a pharmaceutically acceptable salt, solvate or hydrate thereof, can act to kill cancer cells or to control or suppress tumor growth or metastasis, among other functions.

Pharmaceutical formulations based upon halogenated pyrrolopyrimidine and thienopyrimidine compounds of the present invention comprise at least one of the compounds of Formula (I) or Formula (II) or a pharmaceutically acceptable salt, solvate or hydrate thereof, in a therapeutically effective amount for treating cancer optionally in combination with a pharmaceutically acceptable additive, carrier and/or excipient. One of ordinary skill in the art will recognize that a therapeutically effective amount of one of more compounds according to the present invention will vary with the condition to be treated, its severity, the treatment regimen to be employed, the pharmacokinetics of the agent used, as well as the patient (animal or human) treated.

The formulations of the present invention include those suitable for oral, parenteral (including subcutaneous, intradermal, intramuscular, intravenous, intratumoral and intraarticular), rectal and topical (including dermal, buccal, sublingual and intraocular) administration, as well as those for administration by inhalation. The most suitable route may depend upon the condition and disorder of the recipient. Exemplary formulations are well known to those skilled in the art, and general methods for preparing them are found in any standard pharmacy school textbook, for example, Remington: THE SCIENCE AND PRACTICE OF PHARMACY, 21st Ed., Lippincott. The formulations of the present invention may conveniently be presented in unit dosage form and may be prepared by any of the methods well known in the art of pharmacy. All methods include the step of bringing into association a compound or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

The concentration of active compound of the present invention, i.e., at least one of the compounds of Formula (I) or (II) or a pharmaceutically acceptable salt, solvate or hydrate thereof, in the drug composition will depend on absorption, distribution, inactivation, and excretion rates of the drug as well as other factors known to those of skill in the art. It is to be noted that dosage values will also vary with the severity of the condition to be alleviated. The composition may be administered at once, or may be divided into a number of smaller doses to be administered at varying intervals of time.

Oral compositions will generally include an inert diluent or an edible carrier. They may be enclosed in gelatin-capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following non-limiting ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or fruit flavoring. When the dosage unit form is a capsule, it can contain, in addition to any of the above, a liquid carrier such as a fatty oil. In addition, dosage unit forms can contain various other materials which modify the physical form of the dosage unit, for example, coatings of sugar, shellac, or enteric agents.

The active compound may also be administered as a component of an elixir, suspension, syrup, wafer or the like. A syrup may contain, in addition to the active compounds, sucrose or fructose as a sweetening agent and certain preservatives, dyes and colorings and flavors.

In certain embodiments of the present invention, the halogenated pyrrolopyrimidines and thienopyrimidines are formulated as admixture with a pharmaceutically acceptable carrier, excipient or additive. The pharmaceutical composition may be administered via a topical, parenteral, intravenous, intramuscular, transdermal, buccal, subcutaneous, suppository or other route, including an eye or ocular route. Intravenous and intramuscular formulations are generally administered in sterile saline. Of course, one of ordinary skill in the art may modify the formulations within the teachings of the specification to provide numerous formulations for a particular route of administration without rendering the pharmaceutical compositions unstable or compromising their therapeutic activity.

Pharmaceutical compositions containing any of the compounds of Formula (I) or Formula (II) a pharmaceutically acceptable salt, solvate or hydrate thereof, may be conveniently presented in unit dosage form and prepared by any of the methods well known in the art of pharmacy. In general, a therapeutically effective amount of the present preferred compound in dosage form usually ranges from slightly less than about 0.025 mg/kg to about 5 g/kg of body weight, and in certain embodiments about 2.5 mg/kg to about 750 mg/kg of body weight or about 5 mg/kg to about 250 mg/kg of body weight of the patient, depending upon the compound used, the condition being treated and the route of administration, although exceptions to this dosage range may be contemplated by the present invention.

In an embodiment, the present invention is also directed to methods for the treatment of tumors and/or cancer comprising administering an effective amount of one or more halogenated pyrrolopyrimidines and thienopyrimidines of the present invention and/or a pharmaceutically acceptable salt, solvate or hydrate thereof to a patient in need of such therapy. For example, the present invention contemplates methods of treating various cancers and complications thereof. More particularly, the present invention relates to methods for inhibiting the growth of benign and malignant cancer, including a malignant tumor or cancer comprising exposing the tumor to an inhibitory or therapeutically effective amount or concentration of at least one of the halogenated pyrrolopyrimidines and thienopyrimidines or pharmaceutically acceptable salts or pharmaceutically acceptable composition thereof. Treatment of internal malignancies such as eye or ocular cancer, rectal cancer, colon cancer, cervical cancer, prostate cancer, breast cancer, liver cancer and bladder cancer, and age-related cancer among numerous others are contemplated by the present invention.

Accordingly, the compounds and/or compositions of the present invention are useful for treating animals, and in particular, mammals, including humans, as patients. Thus, humans and other animals, and in particular, mammals, suffering from hyperproliferative disorders, and in particular, cancer, or other diseases as disclosed herein, can be treated by administering to the patient an effective amount of one or more of the halogenated pyrrolopyrimidines and thienopyrimidines according to the present invention, or its derivative or a pharmaceutically acceptable salt thereof, optionally in a pharmaceutically acceptable carrier or diluent, either alone, or in combination with other known pharmaceutical agents (depending upon the disease to be treated). Treatment according to the present invention can also be by administration of the compounds and/or compositions of the present invention in conjunction with other conventional cancer therapies, such as radiation treatment or surgery or administration of other anti-cancer agents.

The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer. In particular aspects, the cancer may be a chemo-resistant cancer, i.e., refractive forms of cancer.

The methods and compositions of the present invention further provide combination therapies which can enhance the therapeutic or protective effect of the compounds of the present invention, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. Further, a tissue, tumor, or cell can be contacted with the compounds or compositions of the present invention and one or more additional anti-cancer treatment. For example, an additional anticancer treatment may include a chemotherapeutic agent, radiotherapy, surgical therapy, or immunotherapy.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine, trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-I 1); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Within a single day (24-hour period), the patient may be given one or multiple administrations of the halogenated pyrrolopyrimidines and thienopyrimidines. The course of treatment may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc. Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Preparative Examples

Experimental.

All chemicals and reagents listed in this section were purchased through commercially available sources unless otherwise noted. All reactions run in $CH_2Cl_2$, $CH_3CN$, and THF were obtained from a solvent purification system (SPS, Model: mBraun Labmaster 130). All reactions run in anhydrous DMF, MeOH and pyridine were obtained from Sigma-Aldrich or Acros Organics. All $^1H$ and $^{13}C$ NMR spectra were obtained from a JEOL ECX 400 MHz NMR. All $^1H$ and $^{13}C$ NMR spectra were referenced to internal tetramethylsilane (TMS) at 0.0 ppm. The spin multiplicities are indicated by the symbols s (singlet), d (doublet), dd (doublet of doublets), t (triplet), q (quartet), m (multiplet), and br (broad). All NMR solvents were obtained from Cambridge Isotope Laboratories. All reactions were monitored by thin layer chromatography (TLC) on 0.25 mm precoated glass plates. All column chromatography was run on 32-63 u silica gel obtained from Dynamic Adsorptions Inc. (Norcross, Ga., USA). Melting points are uncorrected. Yields refer to chromatographically and spectroscopically ($^1H$ and $^{13}C$ NMR) homogeneous materials. All mass spectra (MS) were recorded and obtained from the University of Maryland Baltimore County Mass Spectrometry Facility and Johns Hopkins Mass Spectrometry Facility. The FAB mass spectra were obtained using double focusing magnetic sector mass spectrometer equipped with a Cs ion gun and fourier transform ion cyclotron resonance equipped with ESI source.

Example 1 Synthesis of
2,4-Dichlorothieno[3,2-d]pyrimidine (1) (FIG. 1A)

Thieno[3,2-d]pyrimidin-2,4(1H,3H)-dione (4)

In a dry flask methyl-3-amino-2-thiophene carboxylate 3 (5.00 g, 31.80 mmol) was dissolved in acetic acid (100 mL) to obtain a yellow solution to which potassium cyanate (10.31 g, 127.30 mmol) dissolved in water (80 mL) was added dropwise over 3 h. The resultant suspension was stirred overnight (16 hr) at which point the suspension was filtered. The white solid residue was dissolved in 2N NaOH (80 mL) by warming to 70° C. The clear solution was then acidified by AcOH (pH 4-5), the resulting white precipitate was filtered, washed with water then acetone and dried to obtain 4 as a white solid (3.80 g, 22.60 mmol, 71%).

2,4-Dichlorothieno[3,2-d]pyrimidine (1)

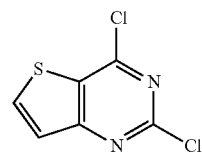

In a dry flask, thieno[3,2-d]pyrimidin-2,4(1H,3H)-dione 4 (4.00 g, 23.78 mmol) was refluxed in freshly distilled $POCl_3$ (50 mL) under nitrogen overnight (16 h) at which point the $POCl_3$ was evaporated and the residue extracted with $CH_2Cl_2$ (50 mL). The organic layer was washed with saturated $NaHCO_3$ solution (50 mL), brine (50 mL), dried over $MgSO_4$ and concentrated. The residue was crystallized from EtOAc to obtain 1 as a pale green-yellow solid (4.00 g, 19.50 mmol, 82%). Mp: 135-137° C. $^1H$ NMR (400 MHz, $CDCl_3$): δ 7.55 (d, J=5.0 Hz), 8.12 (d, J=5.5 Hz). $^{13}C$ NMR (100 MHz, $CDCl_3$): δ 124.6, 129.4, 139.3, 155.8, 156.32, 163.5.

FAB-MS m/z for $C_6H_2Cl_2N_2S$ calculated $[M+H]^+$ 204.9388, found 204.9400 ($2\times^{35}Cl$), 206.9366 ($^{35}Cl$ $^{37}Cl$).

Figure 1B:
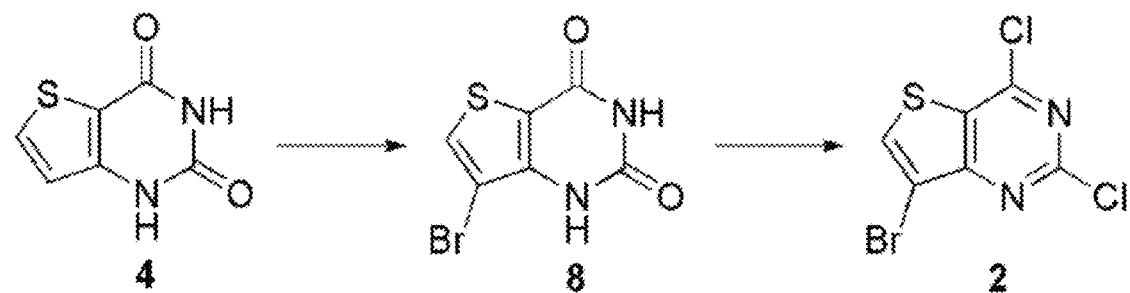

Example 2 Synthesis of Bromo-2,4-dichlorothieno [3,2-d]pyrimidine (FIG. 1B)

7-Bromo-thieno[3,2-d]pyrimidin-2,4 (1H,3H)-dione (8)

To 100 mL glass tube containing thieno[3,2-d]pyrimidin-2,4-dione 4 (5.88 g, 34.86 mmol), AcOH (60 mL) and bromine (3.6 mL, 69.72 mmol) were added and the tube capped. The sealed tube was stirred in a preheated oil bath at 90° C. for 24 h. An additional portion of bromine (3.6 mL, 69.72 mmol) was added to the sealed tube and mixture stirred for another 24 h at 90° C. The AcOH was evaporated to obtain a solid residue to which water was added (200 mL) and the suspension filtered and residue washed repeatedly with water and dried under vacuum to obtain 8 as an off-white solid (8.07 g, 32.67 mmol, 94%). Mp 251.0-252.9° C. $^1$H NMR (400 MHz, DMSO-$d_6$): δ 8.22 (s, $^1$H), 11.40 (br s, NH), 11.58 (br s, 1H, NH). $^{13}$C NMR (100 MHz, DMSO-$d_6$): δ 99.6, 112.1, 133.4, 145.1, 152.1, 159.0. FAB-MS m/z for $C_6H_3BrN_2O_2S$ calculated $[M+H]^+$ 246.9171, found 246.9175 ($^{79}Br$), 248.9161 ($^{81}Br$).

7-Bromo-2,4-dichlorothieno[3,2-d]pyrimidine (2)

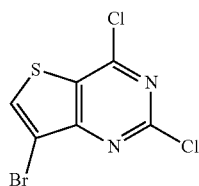

2

To a round bottom flask containing 7-bromothieno[3,2-d]pyrimidin-2,4-dione 8 (4.07 g, 16.47 mmol), DMAP (8.38 g, 68.76 mmol) and freshly distilled POCl$_3$ were added and the suspension stirred at 105-110° C. for 2 h under nitrogen. The POCl$_3$ was evaporated and the residue extracted with CH$_2$Cl$_2$ (300 mL). The organic layer was washed with aq. NaHCO$_3$ (300 mL), brine (200 mL) and dried over MgSO$_4$. The dried organic layer was concentrated, loaded on silica and the product purified using column chromatography eluting with 19:1 hexanes:EtOAc to obtain 2 as a white solid (3.41 g, 12.00 mmol, 73%). $R_f$ 0.5 in 9:1 hexanes/EtOAc. Mp 180.2-183.0° C. $^1$H NMR (400 MHz, CDCl$_3$): δ 8.13 (s, $^1$H). $^{13}$C NMR (100 MHz, CDCl$_3$): δ 160.0, 158.0, 156.0, 135.0, 128.0, 109.5. FAB-MS m/z for $C_6HBrCl_2N_2S$ calculated $[M+H]^+$ 282.8493, found 282.8495 ($2\times^{35}Cl$, $^{79}Br$), 284.8468 ($2\times^{35}Cl$, $^{81}Br$), 286.8443 ($^{35}Cl$, $^{37}Cl$, $^{81}Br$), 288.8419 ($2\times^{37}Cl$, $^{81}Br$).

Figure 2:
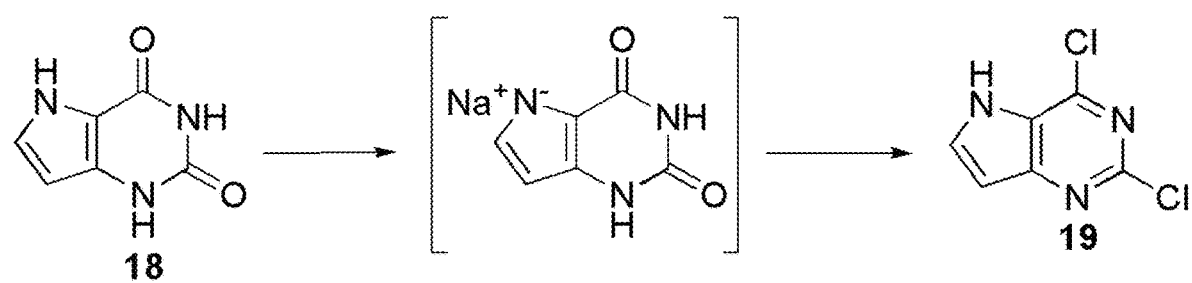
FIG. 2 is a scheme for the synthesis halogenated pyrrolo[3,2-d]pyrimidine (19).

Example 3 Synthesis of Halogenated pyrrolo[3,2-d]pyrimidine (FIG. 2)

Pyrrolo[3,2-d]pyrimidin-2,4-dione (18)

To a stirred slurry of (E)-6-(2-(dimethylamino)vinyl)-5-nitropyrimidin-2,4-dione[35,36] (1 g, 4.4 mol) in fresh glacial AcOH (50 mL), Zinc dust (stabilized) (2 g) was added in two lots of 1 g with an interval of 1 h. Upon overnight stirring the yellow slurry changed to a pale yellow to off-white slurry which was filtered and the filtrate concentrated in vacuo to obtain brown syrup. The product was precipitated from the brown syrup using ethanol to obtain as white solid (0.6 g, 89.8%). The spectral data agrees with reported data. $^1$H NMR (400 MHz, DMSO-$d_6$): δ 5.82-5.83 (t, $^1$H, J=2.28 Hz), 7.12-7.13 (t, $^1$H, J=2.72 Hz, J=2.96 Hz), 10.57 (s, 1H), 10.74 (s, 1H), 11.82 (s, 1H). $^{13}$C NMR (400 MHz, DMSO-$d_6$): δ 96.5, 110.9, 127.4, 135.1, 152.0, 156.3.

2,4-Dichloropyrrolo[3,2-d]pyrimidine (19)

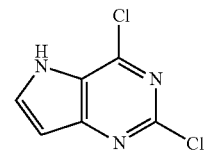

19

To pyrrolo[3,2-d]pyrimidin-2,4-dione 18 (2.00 g, 13.2 mmol), 1 N NaOH (15 mL), and 0.60 g NaOH in 15 mL H$_2$O was added and the mixture stirred at 40° C. until a solution was formed. The solution was then cooled to room temperature (21-25° C.) and then placed in an ice bath to obtain thick slurry. The slurry was then filtered to obtain a pale yellow solid. The solid was dissolved in 1 N NaOH (15 mL), and heated to 40° C. to obtain a clear solution that upon cooling provided white crystals. The crystals were washed with MeOH (20 mL) and acetone (20 mL), and then dried under vacuum. The dry solids were taken in phenylphosphonic dichloride (10 mL) and heated to 170-175° C. for 5 h during which the reaction mixture became a brown-black solution. After 5 h the hot reaction mixture was poured onto ice, extracted with EtOAc (200 mL) and the organic layer washed with sat. NaHCO$_3$ solution (3×100 mL) till all effervescence subsided. The organic layer was then washed with brine and dried over MgSO$_4$. The organic layer was concentrated in vacuo and loaded onto silica. The product was purified using column chromatography eluting with 9:1 then 3:1 hexanes/EtOAc to obtain compound 18 as an off-white solid (1.50 g, 7.9 mmol, 60%). Rf 0.5 in 3:1 hexanes/EtOAc. Mp 228.3-232.0° C. 1H NMR (400 MHz, DMSO-d6): δ 6.71 (d, $^1$H, J=3.2 Hz), 8.09 (d, $^1$H, J=2.8 Hz), 12.75 (s, $^1$H, NH). $^{13}$C NMR (100 MHz, DMSO-d6): d 103.2, 124.3, 138.0, 143.5, 149.6, 153.9. ESI-MS m/z for $C_6H_3Cl_2N_3$ calculated [M+H]+ 187.9776, found 187.9777.

Figure 3A:
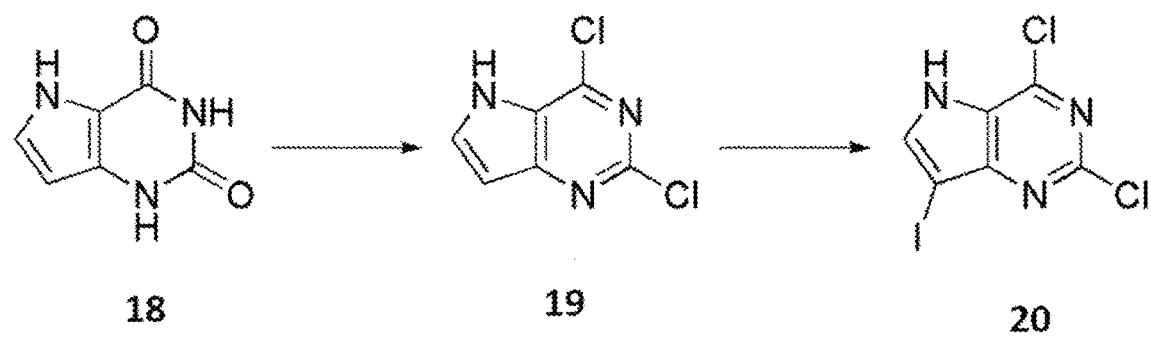
FIG. 3 (A) is a scheme for the synthesis of 7-iodo-2,4-dichloro pyrrolo[3,2-d]pyrimidine (20) FIG. 3 (B) is a scheme for the synthesis of 7-iodo-2,4-bis-benzyloxy-5H-pyrrolo[3,2-d]pyrimidine (16).

Example 4 Synthesis of 7-iodo-2,4-dichloro pyrrolo[3,2-d]pyrimidine (20) FIG. 3A

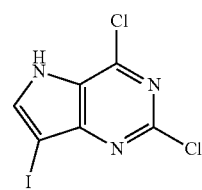 [SMILES: Clc1nc(Cl)c2[nH]cc(I)c2n1]

To a solution of 2,4-dichloro pyrrolo[3,2-d]pyrimidine 19 (100 mg, 0.53 mmol) in anhydrous THF (5 mL), NIS (144 mg, 0.64 mmol) was added under N$_2$ atmosphere and stirred for 2 h after which TLC indicated consumption of 19. The solvent was removed in vacuo and the residue dissolved in EtOAc. The organic phase was washed with aq. solution of Na$_2$S$_2$O$_3$ followed by water, brine and then dried over MgSO$_4$. The organic layer was concentrated in vacuo and loaded on silica. The product 20 was purified using column chromatography eluting with 9:1 hexanes/EtOAc to obtain product as off-white solid (90 mg, 54%). R$_f$ 0.55 in 3:1 hexanes/EtOAc. Mp decomposed from 160-230° C. $^1$H NMR (400 MHz, DMSO-d$_6$): δ 8.29 (s, $^1$H), 13.19 (s, $^1$H). $^{13}$C NMR (400 MHz, DMSO-d$_6$): δ 58.2, 124.4, 140.9, 143.5, 149.8, 153.5. ESI-MS m/z for calculated [M+H]$^+$ 313.8743, found 313.8740.

Figure 3B:
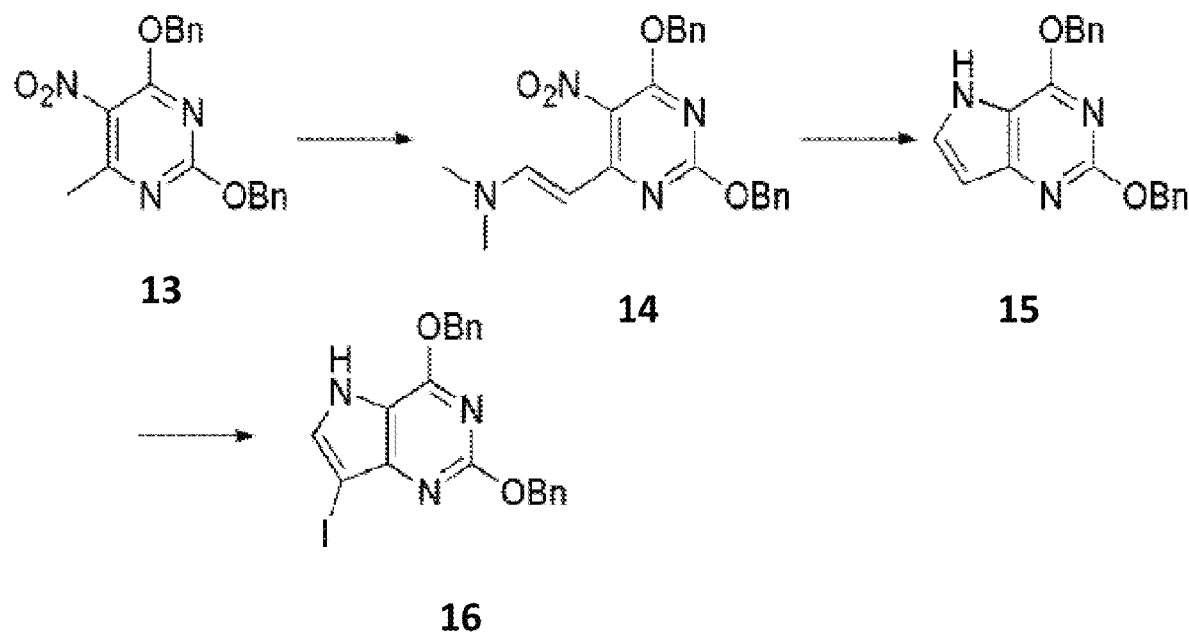

Example 5 Synthesis of 7-iodo-2,4-bis-benzyloxy-5H-pyrrolo[3,2-d]pyrimidine (16) FIG. 3B

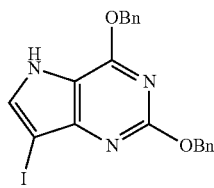 [SMILES: Ic1c[nH]c2c(OCc3ccccc3)nc(OCc3ccccc3)nc12]

2,4-Bis-benzyloxy-5-nitro-6-dimethylaminovinyl pyrimidine (14)

To a solution of 2,4-Bis-O-Benzyl-6-methyl-5-nitro pyrimidine 13 [37] (2.3 g, 6.5 mmol) in DMF (20 mL), DMF-dimethyl acetal (1.74 mL, 13 mmol) was added at room temperature under N$_2$ atmosphere. The reaction was lowered in a preheated oil bath at 60-65° C. and stirred overnight upon which TLC indicated absence of starting material. The solvents were removed and the residue loaded on silica. The product was purified using column chromatography eluting with 9:1 hexanes/EtOAc to obtain product 14 as orange-yellow solid (2 g, 75%). R$_f$ 0.5 in 3:1 hexanes/EtOAc. $^1$H NMR (400 MHz, CDCl$_3$): δ 2.87-2.94 (br d, 6H), 5.33-5.36 (d, 1H, J=12.36 Hz), 5.38 (s, 2H), 5.44 (s, 2H), 7.31-7.41 (m, 10H), 7.98-8.01 (d, 1H, J=12.36 Hz). $^{13}$C NMR (400 MHz, CDCl$_3$): δ 68.9, 69.5, 87.9, 127.5, 128.0, 128.1, 128.3 128.5, 135.8, 136.6, 151.8, 160.7, 161.6, 163.5. FAB-MS for C$_{22}$H$_{22}$N$_4$O$_4$ calculated [M+H]$^+$ 407.1714, found 407.1717.

2,4-Bis-benzyloxy-5H-pyrrolo[3,2-d]pyrimidine (15)

To a suspension of 2,4-Bis-O-Benzyl-5-nitro-6-O-dimethylaminovinyl pyrimidine 14 (2 g, 4.9 mmol) in AcOH (40 ml), Zn (4 g) was added in lot of 2 g with an interval of 4 hrs. The reaction mixture was stirred overnight at room temperature during which a dark yellow suspension became pale yellow suspension. The reaction mixture was filtered and the filtrate concentrated in vacuo to obtain syrup which was dissolved in CH$_2$Cl$_2$ then washed with saturated aq. NaHCO$_3$ followed by brine. The organic phase was dried over MgSO$_4$ and loaded on silica. The product 15 was purified using column chromatography eluting with 4:1 and 1:1 hexanes/EtOAc to obtain product as pale-yellow solid (1.45 g, 90%). R$_f$ 0.3 in 1:3 hexanes/EtOAc. $^1$H NMR (400 MHz, CDCl$_3$): δ 5.47 (s, 2H), 5.54 (s, $^1$H), 6.50-6.51 (dd, 1H, J=1.84, 2.28), 7.29-7.38 (m, 7H), 7.43-7.45 (m, 2H), 7.52-7.53 (m, 2H), 8.41 (br s, 1H, NH). $^{13}$C NMR (400 MHz, CDCl$_3$): δ 68.3, 69.0, 102.6, 111.9, 127.8, 128.3, 128.4, 128.5, 128.6, 128.7, 128.8, 136.1, 137.3, 151.8, 156.79, 159.7. FAB-MS for C$_2$H$_{17}$N$_3$O$_2$ calculated [M+H]$^+$ 332.1394, found 332.1398.

7-iodo-2,4-bis-benzyloxy-5H-pyrrolo[3,2-d]pyrimidine (16)

To a stirred solution of 2,4-bis-O-benzyl-5H-pyrrolo[3,2-d]pyrimidine 15 (1.43 g, 4.3 mmol) in anhydrous CH$_2$Cl$_2$ (15 mL) under N$_2$, NIS (1.069 g, 4.7 mmol) was added at which point the reaction mixture turned from pink to orange. The mixture was stirred overnight until the TLC indicated the absence of starting material. The reaction mixture was washed with aqueous Na$_2$S$_2$O$_3$ (15 mL) followed by brine (15 mL). The organic layer was dried over MgSO$_4$, loaded onto silica and purified using column chromatography eluting with 4:1 then 1:1 hexanes/EtOAc to obtain compound 16 as a pale-yellow solid (1.77 g, 3.88 mmol, 90%). R$_f$ 0.4 in 1:3 hexanes/EtOAc. Mp 157.8-158.4° C. $^1$H NMR (400 MHz, CDCl$_3$): δ 5.53 (s, 4H), 7.32-7.41 (m, 9H), 7.55-7.57 (m, 2H), 8.71 (br s, 1H, NH). $^{13}$C NMR: 57.3, 68.7, 69.3, 111.9, 127.9, 128.3, 128.6, 128.66, 128.7, 128.9, 132.4, 135.8, 137.2, 152.0, 156.9, 160.1. FAB-MS m/z for C$_{20}$H$_{16}$IN$_3$O$_2$ calculated [M+H]$^+$ 458.0360, found 458.0357.

Example 6

Lead compounds 1, 2 and 19 were evaluated for anti-cancer activity at nM to uM concentrations in cellular screens. All three compounds exhibited selective activity against melanoma, breast, colon, and renal cancers (NCI60 cell line) but with little or no activity against non-small cell lung and CNS cancers, as shown in FIG. 4. Two leads, that being compounds 1 and 2, exhibited inhibition by 50% in a 5 dose NCI 60 cell line screen (G150). Although their exact mechanism of action has not been fully elucidated, it is believed that these compounds do not inhibit DNA polymerase or kinases (see Example 12 hereinbelow).

Figure 5A:
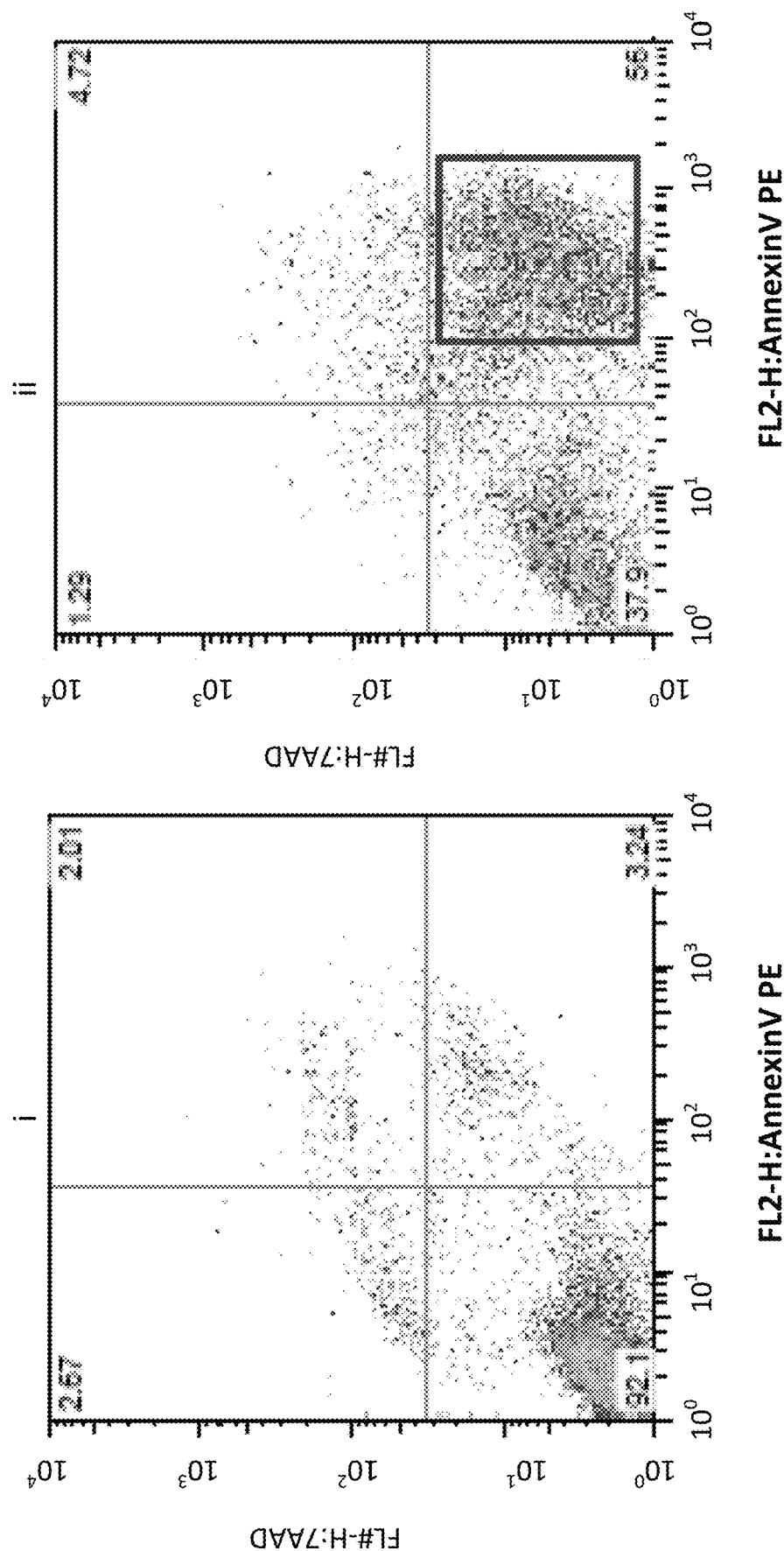
FIG. 5 (A) shows levels of apoptosis of control (i) and compound 1 (ii)
Figure 5B:
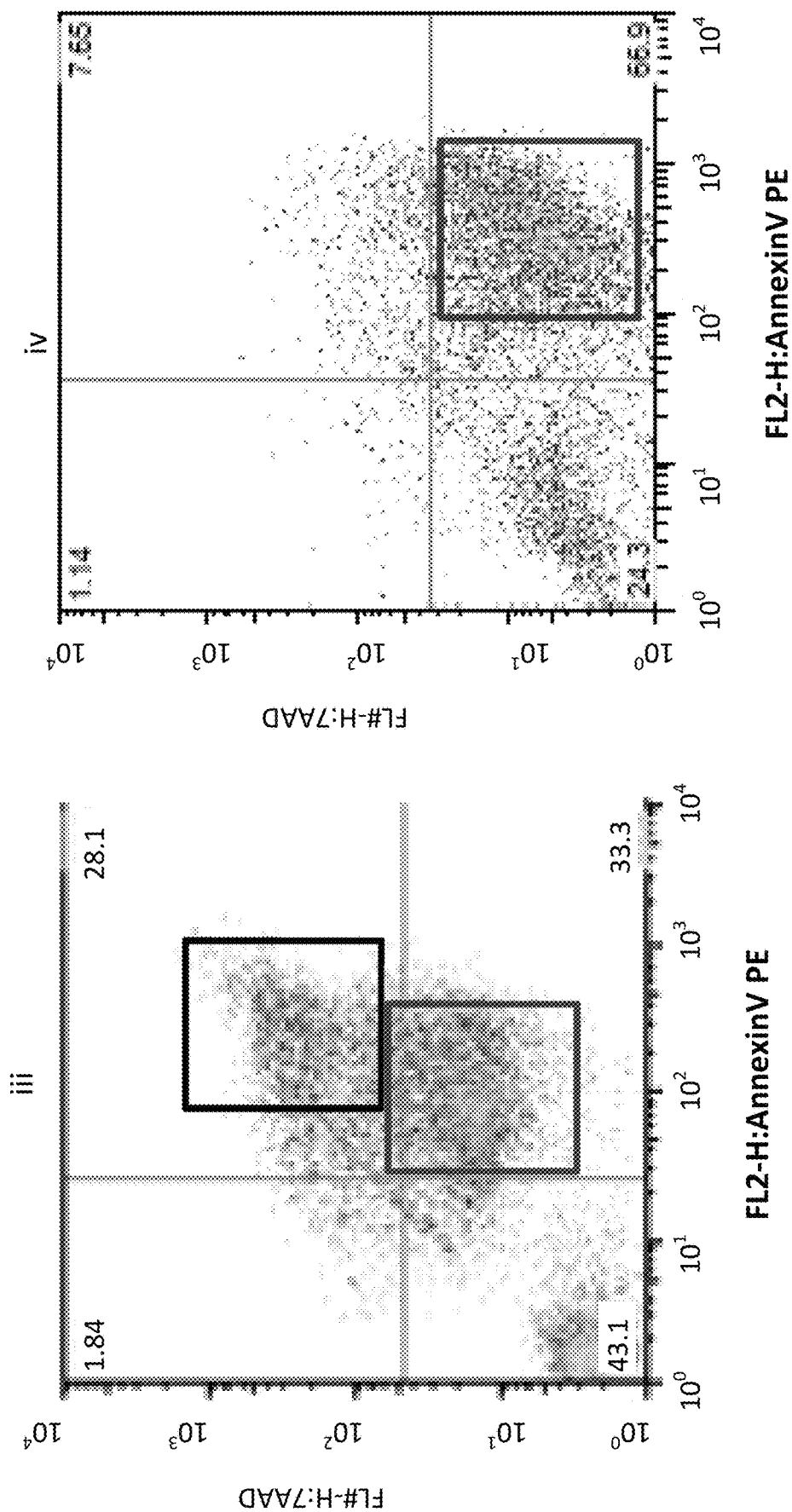

FIGS. 5 A and B contains apoptosis analysis (annexin V staining) in the L1210 leukemia cell line relating to compounds 1 (ii), 2 (iii) and 19 (iv) relative to a control (i). After incubation with 1 μM compound (1) for 48 h, 60% of the cells were observed undergoing apoptotic cell death, with the vast majority of these in early apoptosis (FIG. 5A (ii)). Cell death consistent with apoptosis was also evident in L1210 cells treated with 5.4 μM solution of compound 2 where 55% of cells were Annexin V positive (FIG. 5B (iii), although a larger proportion of these (40%) were consistent with late apoptosis. Compound 19 was incubated for 48 hours in the amount of 1 μM and the compound exhibited 85% apoptosis wherein the majority was early apoptosis. These results of apoptosis assays indicate that compounds 1, 2 and 19 can induce cell death by an apoptotic-like pathway, but in a manner that does not require arrest at a specific stage of the cell cycle.

Example 7

Figure 6:
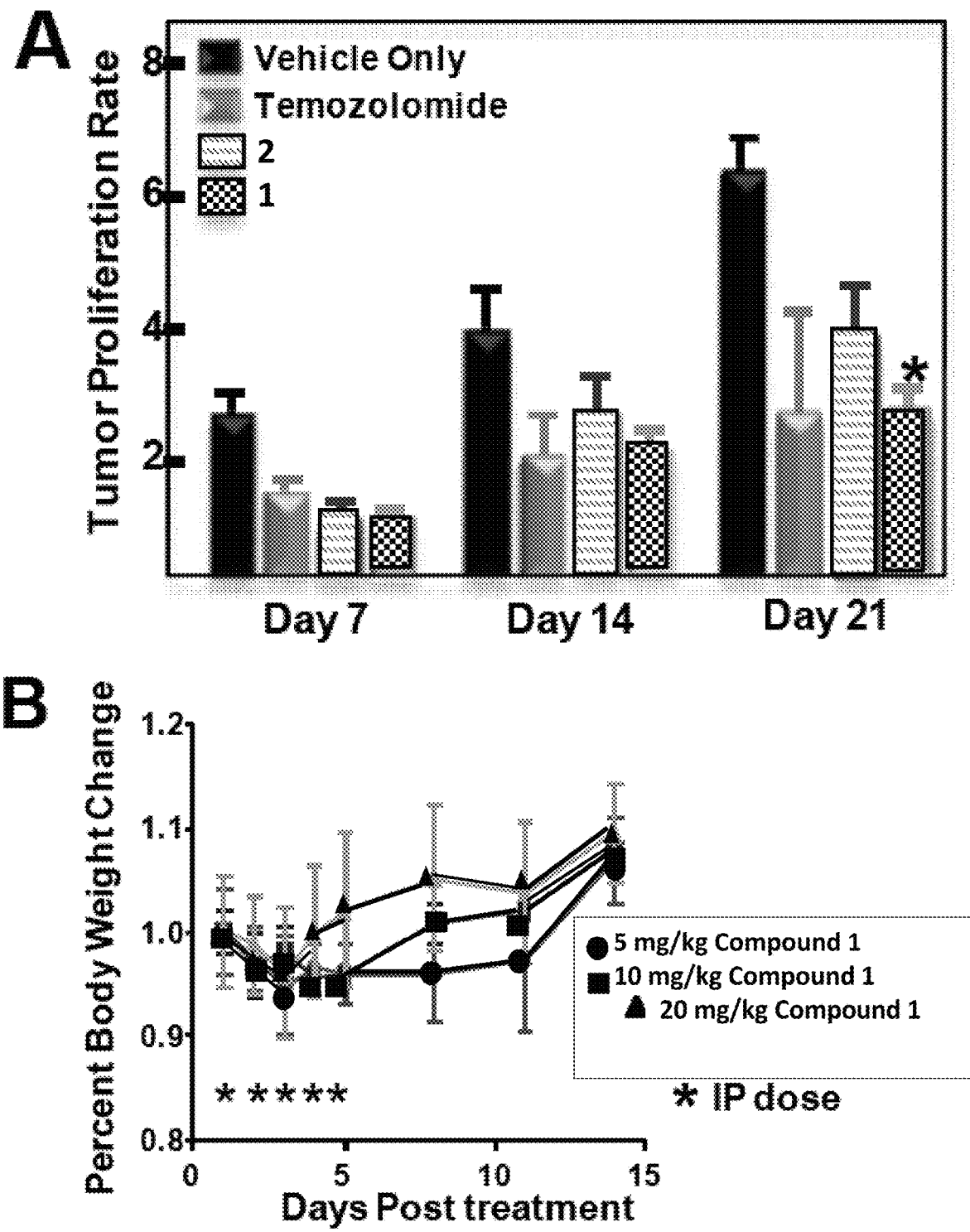
FIG. 6 shows in vivo activity and toxicity of lead compounds 1 and 2, (A) depicts the mean tumor responsiveness in an in vivo activity screen; (B) shows the percent body weight loss versus time for groups of mice receiving IP doses of compound for 5 consecution days.

The selectivity of these pyrimidine analogues for some cancer cell lines suggests that safe and effective doses can be achieved. The histogram in FIG. 6A shows the mean tumor responsiveness ±the SEM in an in vivo activity screen using intra-tumor injection (5 days on/2 days off) in an amount of 0.01 mg/100 mm$^3$ tumor for 21 days. Notably the amount of dosage was based on the size of the tumor because the drug was administered directly into the tumor.

The asterisk denotes p>0.05 when compared to the vehicle only (n=6-10 mice). Melanoma is viewed as resistant to nucleoside analogues, since traditional FDA-approved nucleosides have minimal effects on growth inhibition (100-90% growth percent) and apoptosis (5-10% cell death). Nonetheless, the anti-cancer activity of these leads compound 1 was comparable to the current standard of care, temozolomide, in an in vivo screen as shown in FIG. 6A wherein compound 1 reduced the level of tumor proliferation relative to the temozolomide.

In vivo studies also confirmed that compound 1 was non-toxic when administered systemically. The graph in FIG. 6B shows the percent body weight loss verses time for group (N=3 mice) receiving daily systemic (IP) doses of compound 1 for 5 consecutive days. FVB mice (3 months) received the escalating dose of compound 1 for 5 days.

the cells were counted in a Coulter counter. The $IC_{50}$ (50% inhibitory concentration) was defined as the concentration of the compound that inhibited cell proliferation by 50%. The results of this testing, listed in Table 1, shown below, indicate that the dichloro compounds 19 and 20 had a pronounced effect on proliferation of the all three cell lines. Presence of C7 iodine on the 2,4-dichloro pyrrolo[3,2-d] (compound 20) increases the anticancer activity by a factor of 5 when compared to compound 19. Replacement of the 2,4-chloro with O-benzyl leads to loss of activity by a factor of 3-15, however the activity of compound 16 is comparable to compound 19 alluding to compensation of loss of activity due to substitution with O-benzyl by iodine at C7. This alludes to a) importance of C7-I towards activity against cancer cell lines for the 2,4-O-benzylated analogues (15 and 16).

TABLE 1

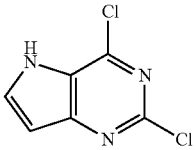

| | | | |
|---|---|---|---|
| L1210 $IC_{50}$ 6.8 ± 2.8 μm | | | L1210 $IC_{50}$ 0.93 ± 0.0 μm |
| CEM $IC_{50}$ 25 ± 2.0 μm | 19 | 20 | CEM $IC_{50}$ 4.9 ± 0.4 μm |
| HeLa $IC_{50}$ 19 ± 3.0 μm | | | HeLa $IC_{50}$ 0.92 ± 0.04 μm |
| L1210 $IC_{50}$ 118 ± 8 μm | | | L1210 $IC_{50}$ 21 ± 2 μm |
| CEM $IC_{50}$ 86 ± 22 μm | 15 | 16 | CEM $IC_{50}$ 17 ± 4 μm |
| HeLa $IC_{50}$ 98 ± 14 μm | | | HeLa $IC_{50}$ 17 ± 0 μm |

When dosing was completed, the mice were monitored for 14 days to determine any toxicity. In mice the best indicator of toxicity is weight loss. Clearly even at 20 mg/kg of body weight, the mice were maintaining their weight, indicating a lack of toxicity. Equally important, this in vivo screen confirmed the results observed in the above described in vitro cell-based activity screens. These data identify that the halogenated pyrrolo- and thienopyrimidine compounds of the present invention as a new class of agents for the treatment of melanoma Example 8

Cell proliferation assays for several of the compounds were performed on L1210, a mouse lymphocytic leukemia cell line [38]; CCRF-CEM [39] an acute lymphoblastic leukemia cell line; and HeLa, a human cancer cell line derived from a human cervical adenocarcinoma. [40] Murine Leukemia L1210, human lymphocytic CEM and human cervix carcinoma HeLa cells were obtained from the American Type Culture Collection (ATCC) (Rockville, Md.). All assays were performed in 96-well microtiter plates. To each well were added (5-7.5)×10⁴ tumor cells and a given amount of the test compound. The cells were allowed to proliferate for 48 h (murine leukemia L1210 cells) or 72 h (human lymphocytic CEM and human cervix carcinoma HeLa cells) at 37° C. in a humidified $CO_2$-controlled atmosphere. At the end of the incubation period, The same testing regime was conducted on Compounds 1 and 2 to determine if such compounds inhibited tumor cell proliferation with the following results:

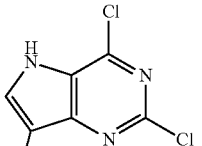

| 1 | 2 |
|---|---|
| L1210 $IC_{50}$  0.67 ± 0.50 μM | 5.4 ± 1.2 μM |
| CEM $IC_{50}$  5.2 ± 1.3 μM | 14 ± 9 μM |
| HeLa $IC_{50}$  3.9 ± 0.5 μM | 4.3 ± 0.2 μM |

Example 9

Evaluation of antimicrobial activity in vitro. Compounds were tested against the following panel of bacteria and fungi purchased from the American Type Culture Collection (ATCC). Briefly, bacteria were grown to mid-log phase, diluted with fresh medium to an optical density at 600 nm ($OD_{600}$) of 0.030-0.060 and then diluted again 1:10. This suspension (195 μL) was added to wells in a 96 well microtiter plate (Sarstedt) and 5 μL of compound dissolved in DMSO was added to give a final concentration of 100-0.1 µM at 2.5% DMSO by volume. A DMSO negative control and standard antibiotic positive controls were included in each plate. All compounds were tested in triplicate for each concentration. Plates were sealed with parafilm, placed in a Ziploc bag to prevent evaporation, and incubated at 30° C. (fungi) or 37° C. (bacteria) for 16-20 hours (48 hours for *C. neoformans*). The $OD_{600}$ values for each well were determined with a plate reader (Biotek, EL800) and the data were standardized to the DMSO control wells after subtracting the background from blank medium. Initial single concentrations were tested at 100 µM and active compounds were further tested with at least nine concentrations for a full dose response. Dose response curves were generated using GraphPad Prism 5 software and used to determine the $MIC_{95}$ concentrations (minimal concentration that inhibits 95% of growth). Compounds 1, 2, 5 and 19 were screened for growth inhibition activity against a panel of bacteria and fungi at a concentration of 100 as shown in Table 2. Compound 5 was included to test the importance of the C4-Cl substituent for activity across a broader range of biological systems. Compounds 1 and 2 exhibited activity against several pathogenic yeast strains (55-99% growth inhibition) and compound 1 also showed weak activity against *Bacillus subtilis*. In addition, compound 1 displayed a higher potency than 2 against several clinical strains of *Cryptococcus neoformans*.

Compounds 1 and 2 were further tested against the susceptible fungal strains to determine the $MIC_{95}$ values. Although the spectrum of anti-microbial activity for compound 1 is broad (Table 3), the bromo analogue 2 is much more selective towards fungi and 2-5 times more potent than compound 1 (Table 3).

TABLE 3

Antifungal activity of thieno[3,2-d]pyrimidines 1 and 2.

| | $MIC_{95}$ (µM) | |
|---|---|---|
| Strain | 1 | 2 |
| C. albicans ATCC 10231 | 23.4 | 10.7 |
| C. neoformans JEC20 | 16.6 | 5.8 |
| C. neoformans B4546 | 34.6 | 7.0 |

$MIC_{95}$—minimum concentration for inhibition by 95%

TABLE 2

Antimicrobial screening of thieno[3,2-d]pyrimidines.

| | | % inhibition at 100 µM | | | |
|---|---|---|---|---|---|
| Microbial strain | strain designation | 1 | 2 | 5 | 19 |
| Bacterial strains | | | | | |
| *Escherichia coli* | ATCC 25922 | NA | NA | NA | NA |
| *Bacillus subtilis* | ATCC 6633 | 43% | NA | NA | NA |
| *Staphylococcus aureus* subsp. *aureus* (MRSA) | ATCC 43300 | NA | NA | NA | NA |
| *Enterococcus faecalis* (FRE) | ATCC 51299 | NA | NA | NT | NT |
| *Pseudomonas aeruginosa* | ATCC 27853 | NA | NA | NT | NT |
| Fungal strains | | | | | |
| Candida albicans | ATCC 10231 | 99% | 99% | NA | NA |
| Cryptococcus neoformans | ATCC 66031 | 101% | 55% | NA | NA |
| C. neoformans | JEC20 | 100% | 91% | NA | NA |
| C. neoformans | VANC-R265 | 93% | 67% | NA | NA |
| C. neoformans | B4546 | 96% | 82% | NA | NA |

NA—No activity,
NT: Not tested

Example 10

Cell-cycle and apoptosis studies were conducted in MDA-MB-231 cells. Cell-cycle analysis of compound 19 at 15 µM concentration lead to arrest of 60% cells in G2/M stage. Similarly, at 1.75 µM concentration, compound 20 arrested 30% of cells in G2/M stage. These results allude to the reduction in ability to arrest cells in G2/M stage upon introduction of iodine at C7. To evaluate the possible mechanism for arrest of cell proliferation, cell-cycle distribution was measured using propidium iodide staining and flow cytometry. While compound 19 is clearly toxic to MDA-MB-231 cells at the tested concentration, only a modest (although statistically significant) increase in annexin V-positive cells was detected. There are several possibilities that could account for this, including: (i) that cell lysis occurs rapidly following induction of apoptosis, preventing significant accumulation of annexin V-positive bodies, or (ii) that a distinct cell death pathway is triggered by compound 19. On the other hand treatment with compound 20 induced robust accumulation of annexin V-positive cells consistent with apoptotic cell death in a manner that is similar to the effects that were observed for thieno[3,2-d]pyrimidines compound 1 and 2.

Figure 9:
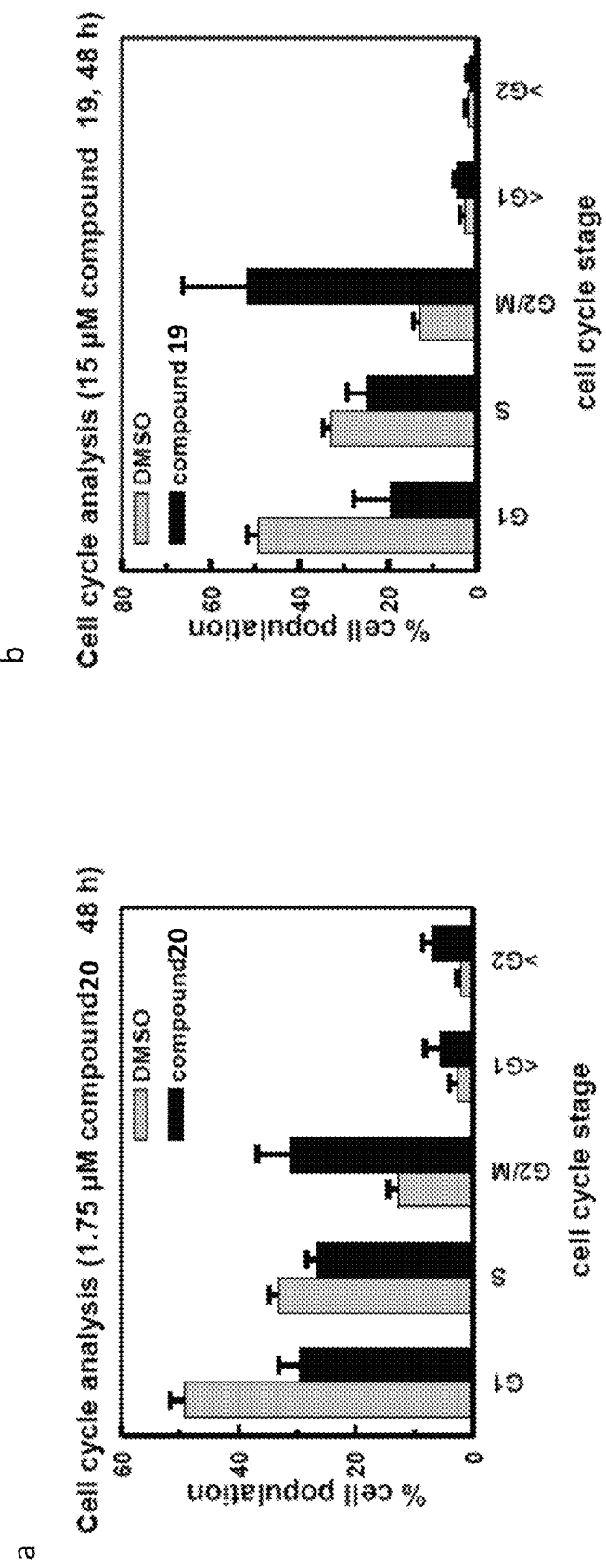
FIG. 9 shows the cell cycle distributions of L1210 cells following 48 hours in the presence of a. 1.75 µM compound 20, b. 15 µM compound 19, and analyzed by flow cytometry of fixed, propidium iodide-stained cells. A minimum of 3000 cells were analyzed per cell population. Each bar represents the mean±SD across 4 independent cell samples.

This study, besides establishing the antiproliferative properties of the 4-Cl pyrrolo[3,2-d]pyrimidines also establishes the effect of C7 iodine on the enhancement of antiproliferative properties; particularly the cytotoxicity manifested by compound 20 against select cancer cell lines. These results have identified antitumor activities of 2,4-dichloro pyrrolo[3,2-d]pyrimidines with emphasis on C7 iodine towards enhancing the potency. These studies establish the use of halogenated pyrrolo[3,2-d]pyrimidines as pharmacologically useful scaffold. These halogenated compounds manifest antitumor activity against cancer by inducing apoptosis via arrest of cell-cycle in G2/M, as shown in FIG. 9.

Example 11

Figure 7:
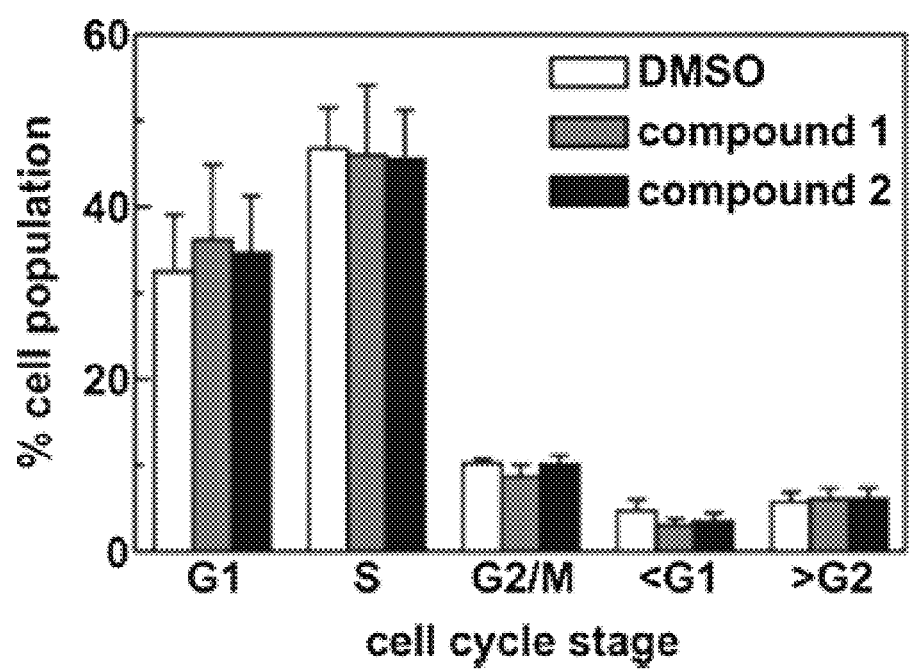
FIG. 7 shows the cell cycle distributions of L1210 cells following 0, 24, or 48 hours in the presence of a. 0.32 µM compound 1, b. 5.4 µM compound 2, and analyzed by flow cytometry of fixed, propidium iodide-stained cells. A minimum of 3000 cells were analyzed per cell population. Each bar represents the mean±SD across 4 independent cell samples.

Many antineoplastic compounds arrest cell proliferation by activating specific checkpoints that block progression through the cell cycle. To test whether compounds 1 or 2 inhibited cell proliferation by this mechanism, their effects on L1210 cell cycle distributions were monitored using propidium iodide staining and flow cytometry (FIG. 7). Cell cycle and apoptosis studies were conducted on L1210, a mouse lymphocytic leukemia cell line obtained from the American Type Culture Collection and grown in Dulbecco's Modified Eagle's Medium (DMEM) plus 10% fetal bovine serum (FBS). $2\times10^6$ cells were seeded in 100 mm dishes and treated with vehicle alone or compounds 1 or 2 at the $IC_{50}$ values determined by cell viability assays or an equivalent volume of DMSO. At 24 and 48 h following treatment the cells were collected, fixed, and stained with propidium iodide (Sigma Aldrich) immediately before analysis by flow cytometry. Vehicle-treated cells were largely confined to G1 and S phases, with very small (<5%) subpopulations in the G2/M phase or showing sub-(<G1) or super-genomic (>G2) DNA content. Surprisingly, 24 h or 48 h treatment with $IC_{50}$ concentrations of either compound 1 or 2 yielded no substantial changes in L1210 cell cycle distribution, indicating that these reagents do not suppress cell growth by activating cell cycle checkpoint mechanisms. This cell cycle assay and the apoptosis assay discussed in Example 6 indicate that both compounds 1 and 2 can induce cell death by an apoptotic-like pathway, but in a manner that does not require arrest at a specific stage of the cell cycle.

Example 12

The thieno[3,2-d]pyrimidine scaffold has been used extensively in the design of kinase inhibitors. To determine if the halogenated compounds of the present invention exhibited the same results, compounds 1 and 2 were screened against twenty kinases at 5 µM using Invitrogen's Select Screen kinase profiling [41] service to explore the possibility of kinase inhibition. Surprisingly they did not exhibit any substantial inhibitory activity against any of the twenty tested kinases and the results of such testing are shown in Table 4.

TABLE 4

: Inhibition of protein kinases by 2,4-dichloro thieno[3,2-d]pyrimidine at 5 µM

| Kinase tested | % inhibition |
| --- | --- |
| FRAP1 (mTOR) | <40% |
| JAK1, JAK2, JAK2 JHI JH2, JAK2 JH1 JH2 V617F, JAK3 | <40% |
| LTK (TYK1), TYK2 | <40% |
| MET (cMet) | <40% |
| PRKCN (PKD3), PRKD1 (PKC mu), PRKD2 (PKD2) | <40% |
| SRC, SRC N1 | <40% |
| PIK3C2A, PIK3C2B, PIK3C3, PIK3CA/PIK3R1, PIK3CD/PIK3R1, PIK3CG | <40% |

Example 13

Human metastatic breast cancer MDA-MB-231 cells were obtained from the American Type Culture Collection (ATCC) (Rockville, Md.) and maintained in Dulbecco's Modified Eagle's Medium (DMEM) containing 10% fetal bovine serum (FBS) without antibiotics at 37° C. in a humidified, $CO_2$-controlled incubator. The cytotoxicity of compounds 1 and 2 was assessed by reduction of 3-(4, 5-dimethylthiazol-2-yl)-2,5-diphenyltetrazolium bromide (MTT). MDA-MB-231 cells were seeded in 96-well plates at $5\times10^3$ cells per well and treated with a range of drug concentrations. After 48 hours, cell viability was measured using the MTT Cell Proliferation Assay kit (ATCC) according to the manufacturer's instructions. Percent cell viability was plotted as a function of drug concentrations and analyzed using a sigmoidal dose response function with PRISM v3.03 software (GraphPad) to resolve drug concentrations yielding 50% cell death ($IC_{50}$). The cell cycle distributions of MDA-MB-231 cells treated with compounds 1 or 2 were analyzed using propidium iodide staining and flow cytometry. $2\times10^6$ cells were seeded in 100 mm dishes and treated with compounds 1 or 2 at the $IC_{80}$ values determined by cell viability assays or an equivalent volume of DMSO. 48 h following treatment the cells were collected, fixed, and stained with propidium iodide (Sigma Aldrich) immediately before analysis by flow cytometry.

Figure 8:
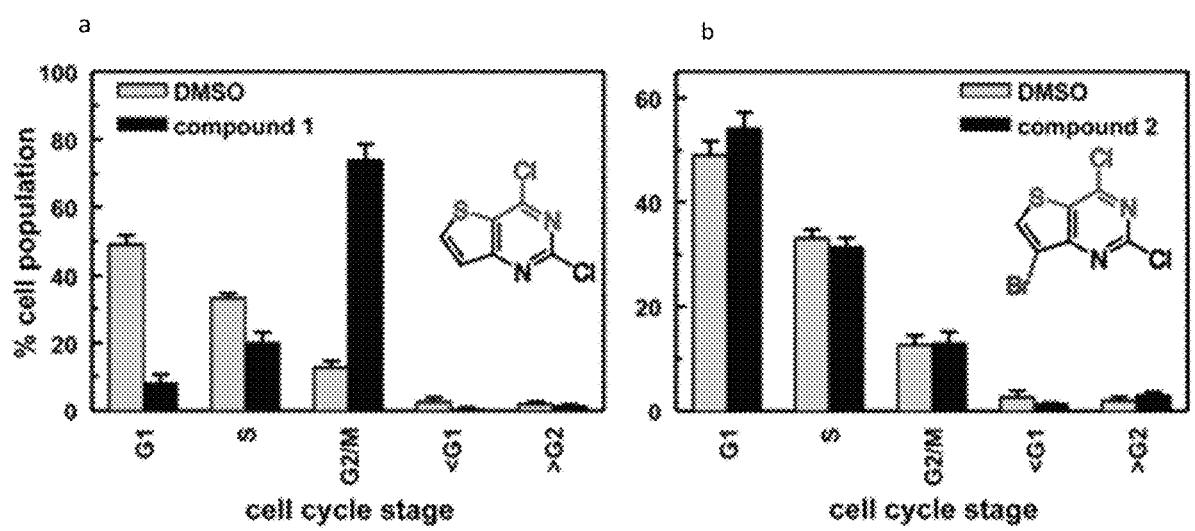
FIG. 8 shows the Cell cycle analyses of MDA-MB-231 cells following treatment with compounds 1 and 2. Cell cycle distributions of MDA-MB-231 cells after 48 hours in the presence of equitoxic (IC$_{80}$) doses of (a) compound 1 (15 µM) or (b) compound 2 (8 µM) analyzed by flow cytometry of fixed, propidium iodide-stained cells and compared to vehicle controls (DMSO). A minimum of 3000 cells were analyzed per cell population. Each bar represents the mean±SD across 4 independent cell samples.

As shown in Example 11, compounds 1 and 2 both induced apoptosis but involving a mechanism independent of cell cycle arrest [42]. To test whether the toxicity of these agents for MDA-MB-231 cells proceeded via a similar pathway, their effects were monitored on cell cycle distributions using propidium iodide staining and flow cytometry. Cumulatively over 80% of vehicle-treated MDA-MB-231 cells were confined to G1 and S phases, with much smaller subpopulations recovered in G2/M (10%) or in cells showing <G1 (<3%) or >G2 (<3%) DNA content (FIG. 8). Treating MDA-MB-231 cells with compound 2 had no effect on their cell cycle distribution, consistent with observations in the L1210 line. However, after treating MDA-MB-231 cells with compound 1, the vast majority (>70%) accumulated in the G2/M phase of the cell cycle. Cell subpopulations in G1 and S phases were concomitantly depleted while no changes were observed in the fraction of cells with <G1 or >G2 DNA content. This dramatic accumulation of cells in G2/M indicates that compound 1, but not compound 2, triggers mitotic arrest in MDA-MB-231 cells.

Example 14

Figure 10:
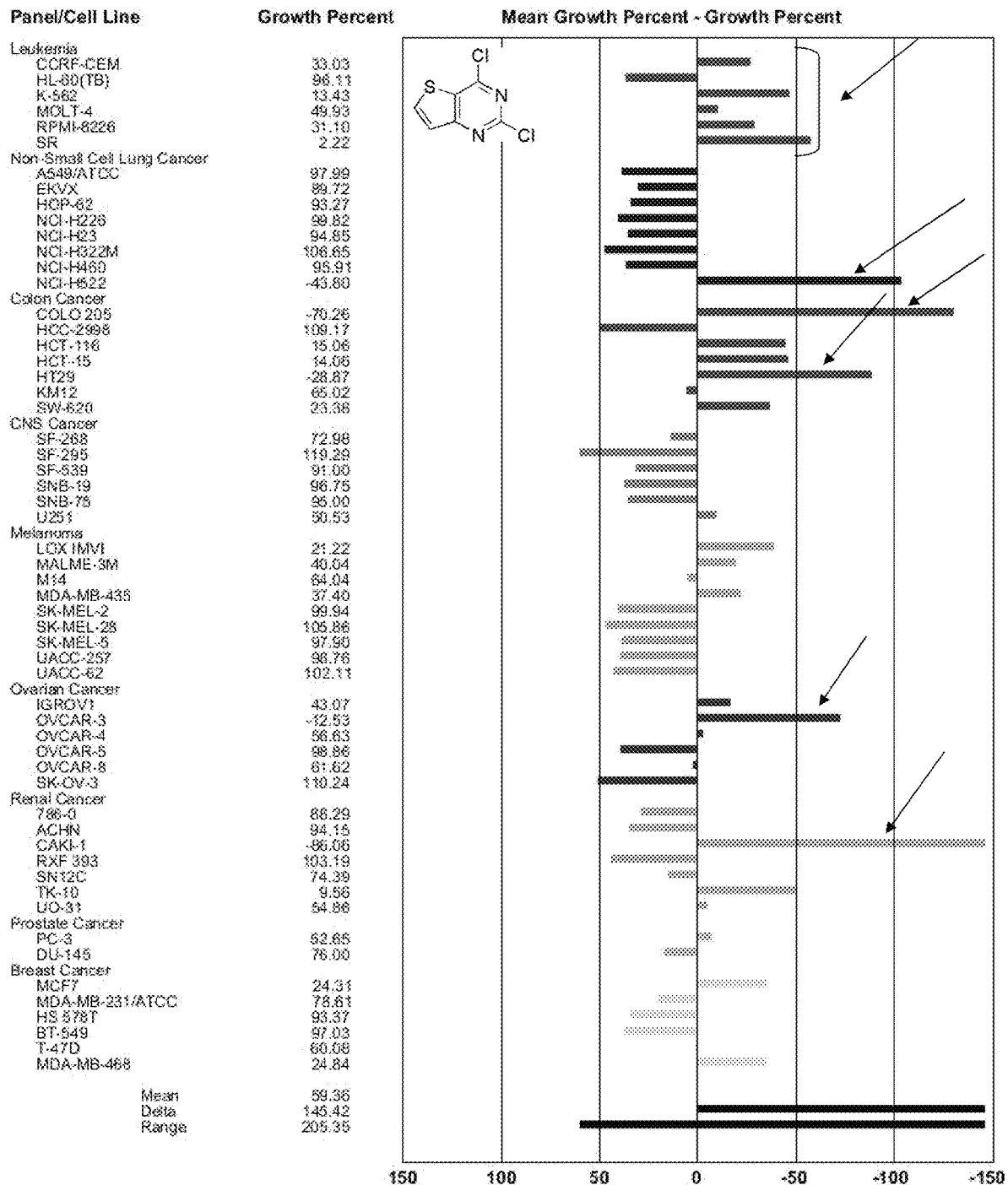
FIG. 10 shows the results of anti-cancer activity of compound 1 and the growth percent of representative cancer cell line from the NCI60 cell line (1 dose).
Figure 11:
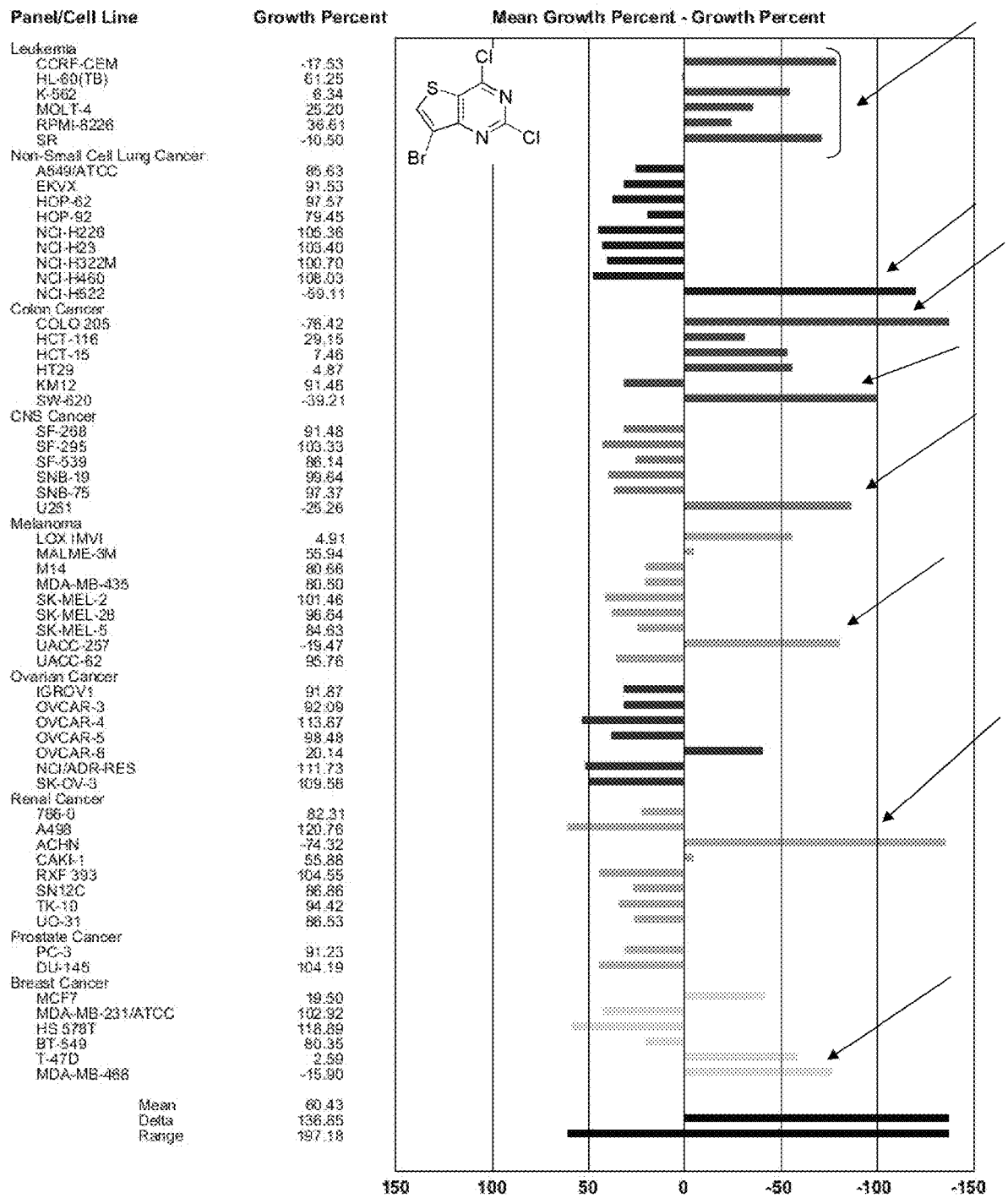
FIG. 11 shows the results of anti-cancer activity of lead compound 2 and the growth percent of representative cancer cell line from the NCI60 cell line (1 dose).
Figure 12:
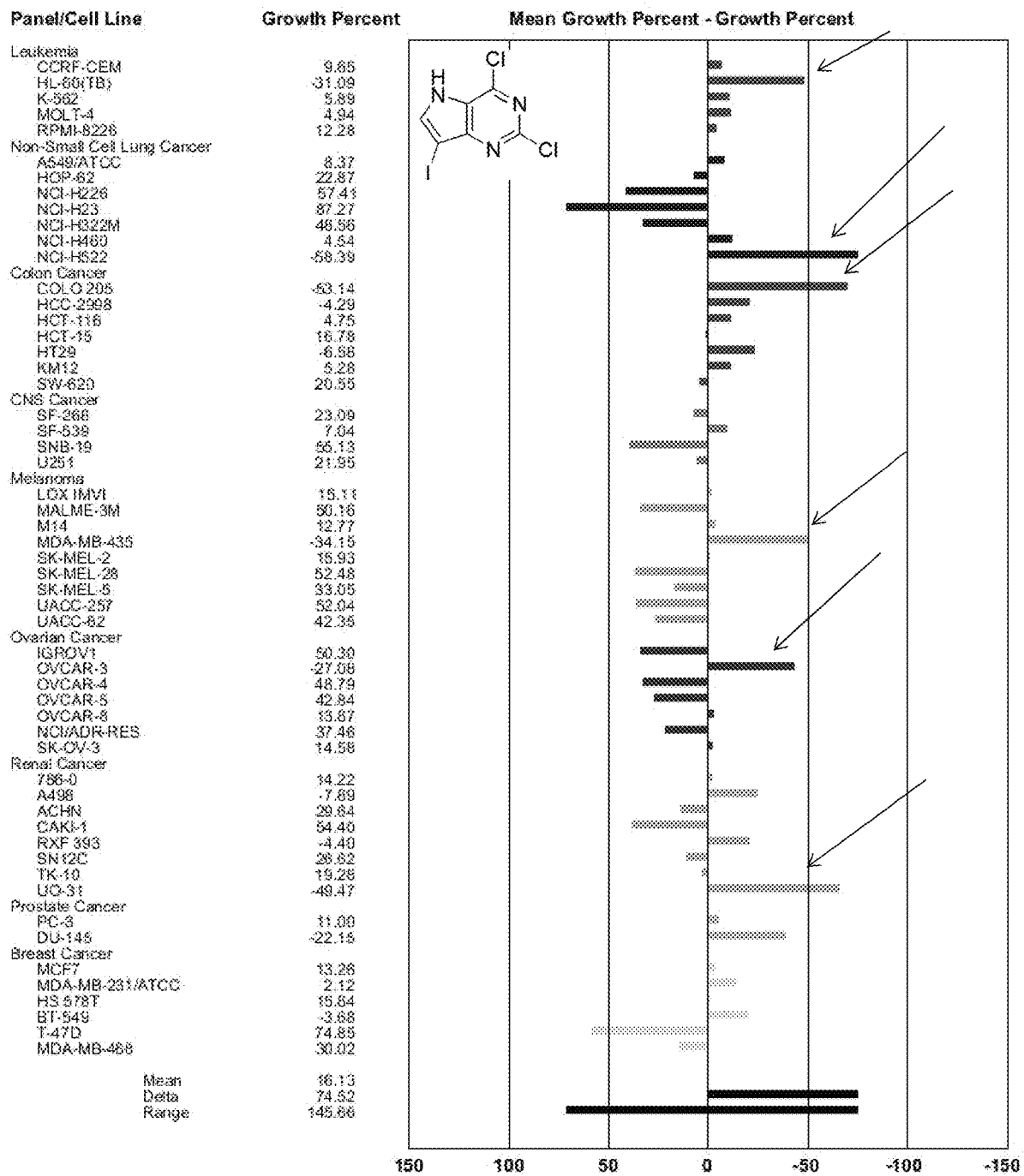
FIG. 12 shows the results of anti-cancer activity of lead compound 19 and the growth percent of representative cancer cell line from the NCI60 cell line (1 dose).

The lead halogenated pyrrolopyrimidines and thienopyrimidines of the present invention were tested in the human cell line screen which is composed of 60 different human tumor cell lines (NCI-60) representing leukemia, melanoma, lung cancer, colon cancer, brain cancer, ovary cancer, breast cancer, prostate cancer and kidney cancer. Testing specifics can be found at the National Cancer Institute at http://dtp.nci.nih.gov/branches/btb/ivelsp.html. Compounds 1, 2 and 19 were testing initially at a single dose ($10^{-5}$M) in the full cell panel. The results of the one-dose are reported as a mean graph of the percent of the growth of the treated cells. Both growth inhibition (values between 0 and 100) and lethality (values less than 0) are detectable. To evaluate the test results, a value of 100 means no growth inhibition. A value of 40 would mean 60% growth inhibition. A value of zero means no net growth over the course of the experiment. A value of −40 means 40% lethality and a value of −100 means all the cells are dead. FIG. 10 shows the one dose results for compound 1, FIG. 11 shows the one dose results of compound 2 and FIG. 12 shows the one dose results of compound 19. The cells with high lethality are emphasized with an arrow in the one dose compilation of results shown in FIGS. 10, 11 and 12. The results of the 5 dose screening are shown in FIG. 13.

REFERENCES

The contents of all references cited herein are incorporated by reference herein for all purposes.
1. Hoelder, S., P. A. Clarke, and P. Workman, Discovery of small molecule cancer drugs: successes, challenges and opportunities. *Mol Oncol.* 6(2): p. 155-76.
2. Flaherty, K. T., Chemotherapy and targeted therapy combinations in advanced melanoma. *Clin Cancer Res*, 2006. 12(7 Pt 2): p. 2366s-2370s.
3. Bastos, D. A., et al., Combination therapy in high-risk stage II or stage III colon cancer: current practice and future prospects. *Ther Adv Med Oncol.* 2(4): p. 261-72.
4. Braun, M. S. and M. T. Seymour, Balancing the efficacy and toxicity of chemotherapy in colorectal cancer. *Ther Adv Med Oncol.* 3(1): p. 43-52.
5. Haggar, F. A. and R. P. Boushey, Colorectal cancer epidemiology: incidence, mortality, survival, and risk factors. *Clin Colon Rectal Surg*, 2009. 22(4): p. 191-7.
6. Pasetto, L. M., et al., FOLFOX versus FOLFIRI: a comparison of regimens in the treatment of colorectal cancer metastases. *Anticancer Res*, 2005. 25(1B): p. 563-76.
7. Alcindor, T. and N. Beauger, Oxaliplatin: a review in the era of molecularly targeted therapy. *Curr Oncol.* 18(1): p. 18-25.
8. Nandan, M. O. and V. W. Yang, An Update on the Biology of RAS/RAF Mutations in Colorectal Cancer. *Curr Colorectal Cancer Rep.* 7(2): p. 113-120.
9. Tan, C. and X. Du, KRAS mutation testing in metastatic colorectal cancer. *World J Gastroenterol.* 18(37): p. 5171-80.
10. Ren, W. R., K V B.; Klein, R S, Convenient synthesis of substituted 3-aminothiophene-2-carbonitriles from α-acetylenic nitriles and their conversion to thieno[3,2-d]pyrimidines. *J. Heterocycl. Chem*, 1986 (23): p. 1757-1763.
11. Amarnath, V. M., R, Survey of methods for the preparation of pyrrolopyrimidines. *Synthesis* 1974: p. 83-859.
12. Lim, M. K., R S; Fox, J J, Synthesis of the pyrrolo[3,2-d]pyrimidine C-nucleoside isostere of inosine. *Tet. Lett*, 1980 (21): p. 1013-1016.
13. Ren, W. L., M I; Otter, B A; Klein, R S, Synthetic studies of the thieno[3,2-d]pyrimidine C-nucleoside isostere of inosine. *J. Org. Chem.*, 1982 (47): p. 4633-4637.
14. Lim, M. K., R S, Synthesis of "9-deazaadenosine"; a new cytotoxic C-nucleoside isostere of adenosine. *Tet. Lett.*, 1981 (22): p. 25-28.
15. Lim, M. R., W Y; Otter, B A; Klein, R S, Synthesis of "9-deazaguanosine" and other new pyrrolo[3,2-d]pyrimidine C-nucleosides. *J. Org. Chem.*, 1983 (48): p. 780-788.
16. Russell, R. K., et al., Thiophene systems. 9. Thienopyrimidinedione derivatives as potential antihypertensive agents. *J Med Chem*, 1988. 31(9): p. 1786-93.
17. Crespo, M. I., et al., Design, synthesis, and biological activities of new thieno[3,2-d] pyrimidines as selective type 4 phosphodiesterase inhibitors. *J Med Chem*, 1998. 41(21): p. 4021-35.
18. Seley, K. L., et al., Synthesis and antitumor activity of thieno-separated tricyclic purines. *J Med Chem*, 2000. 43(25): p. 4877-83.
19. Sutherlin, D. P., et al., Discovery of a potent, selective, and orally available class I phosphatidylinositol 3-kinase (PI3K)/mammalian target of rapamycin (mTOR) kinase inhibitor (GDC-0980) for the treatment of cancer. *J Med Chem*. 54(21): p. 7579-87.
20. Sutherlin, D. P., et al., Discovery of (thienopyrimidin-2-yl)aminopyrimidines as potent, selective, and orally available pan-PI3-kinase and dual pan-PI3-kinase/mTOR inhibitors for the treatment of cancer. *J Med Chem.* 53(3): p. 1086-97.
21. Showalter, H. D., et al., Tyrosine kinase inhibitors. 16. 6,5,6-tricyclic benzothieno[3, 2-d]pyrimidines and pyrimido[5,4-b-] and -[4,5-b]indoles as potent inhibitors of the epidermal growth factor receptor tyrosine kinase. *J Med Chem*, 1999. 42(26): p. 5464-74.
22. Ife, R. J., et al., Reversible inhibitors of the gastric (H+/K+)-ATPase. 5. Substituted 2,4-diaminoquinazolines and thienopyrimidines. *J Med Chem*, 1995. 38(14): p. 2763-73.
23. Safina, B. S., et al., Discovery of novel PI3-kinase delta specific inhibitors for the treatment of rheumatoid arthritis: taming CYP3A4 time-dependent inhibition. *J Med Chem.* 55(12): p. 5887-900.
24. Golub, A. G., et al., Synthesis and biological evaluation of substituted (thieno[2,3-d]pyrimidin-4-ylthio)carboxylic acids as inhibitors of human protein kinase CK2. *Eur J Med Chem.* 46(3): p. 870-6.
25. Zeng, S., et al., Discovery of potent dipeptidyl peptidase IV inhibitors through pharmacophore hybridization and hit-to-lead optimization. *Bioorg Med Chem.* 21(7): p. 1749-55.

26. Temburnikar, K., K. Brace, and K. L. Seley-Radtke, Synthesis of 2'-deoxy-9-deaza nucleosides using Heck methodology. *J Org Chem.* 78(14): p. 7305-11.
27. Temburnikar, K., Z. Zhang, and K. Seley-Radtke, Modified synthesis of 3'-O-TBDPS-protected furanoid glycal. *Nucleosides Nucleotides Nucleic Acids.* 31(4): p. 319-27.
28. Pedeboscq, S., et al., Synthesis and evaluation of apoptosis induction of thienopyrimidine compounds on KRAS and BRAF mutated colorectal cancer cell lines. *Bioorg Med Chem.* 20(22): p. 6724-31.
29. Zong, W. X., et al., Alkylating DNA damage stimulates a regulated form of necrotic cell death. *Genes Dev,* 2004. 18(11): p. 1272-82.
30. Chandra, S., and Pavlick, A. C. (2012) Targeted therapies for metastatic melanoma, *Dermatologic clinics* 30, 517-524.
31. Jang, S., and Atkins, M. B. (2013) Which drug, and when, for patients with BRAF-mutant melanoma?, *The lancet oncology* 14, e60-e69.
32. Das Thakur, M., Salangsang, F., Landman, A. S., Sellers, W. R., Pryer, N. K., Levesque, M. P., Dummer, R., McMahon, M., and Stuart, D. D. (2013) Modelling vemurafenib resistance in melanoma reveals a strategy to forestall drug resistance, *Nature.*
33. Jordan, E. J., and Kelly, C. M. (2012) Vemurafenib for the treatment of melanoma, *Expert opinion on pharmacotherapy* 13, 2533-2543.
34. Maio, M., Di Giacomo, A. M., Robert, C., and Eggermont, A. M. (2013) Update on the role of ipilimumab in melanoma and first data on new combination therapies, *Current opinion in oncology* 25, 166-172.
35 Bourke, D. G.; Burns, C. J.; Cuzzupe, A. N.; Feutrill, J. T.; Kling, M. R.; Nero, T. L.; (Cytopia Research Pty Ltd, Australia). Application: WO WO, 2009, p 130 pp.
36. Guimaraes, C. R. W.; Kopecky, D. J.; Mihalic, J.; Shen, S.; Jeffries, S.; Thibault, S. T.; Chen, X.; Walker, N.; Cardozo, M. *J. Am. Chem. Soc.* 2009, 131, 18139-18146.
37. Evans, G. B.; Furneaux, R. H.; Hutchison, T. L.; Kezar, H. S.; Morris, P. E., Jr.; Schramm, V. L.; Tyler, P. C. *J. Org. Chem.* 2001, 66, 5723-5730.
38. Law, L. W.; Dunn, T. B.; et al. *J. Natl. Cancer. Inst.* 1949, 10, 179-192.
39. Foley, G. E.; Lazarus, H.; Farber, S.; Uzman, B. G.; Boone, B. A.; McCarthy, R. E. *Cancer* 1965, 18, 522-529.
40. Scherer, W. F.; Syverton, J. T.; Gey, G. O. *J. Exp. Med.* 1953, 97, 695-710.
41. Mollard, A.; Warner, S. L.; Call, L. T.; Wade, M. L.; Bearss, J. J.; Verma, A.; Sharma, S.; Vankayalapati, H.; Bearss, D. J. Design, Synthesis, and Biological Evaluation of a Series of Novel AXL Kinase Inhibitors. *ACS Med. Chem. Lett.* 2011, 2, 907-912.
42. Temburnikar, K. W.; Zimmermann, S. C.; Kim, N. T.; Ross, C. R.; Gelbmann, C.; Salomon, C. E.; Wilson, G. M.; Balzarini, J.; Seley-Radtke, K. L. *Bioorg. Med. Chem.* 2014, 22, 2113-2122.
43. Chavez Kathryn, J.; Garimella Sireesha, V.; Lipkowitz, S. *Breast disease* 2010, 32, 35-48.

That which is claimed is:

1. A pharmaceutical composition comprising (i) an effective amount of a halogenated thienopyrimidine compound having the formula:

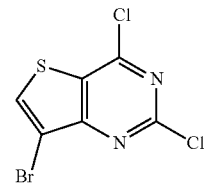 [SMILES: Clc1nc(Cl)c2[nH]cc(I)c2n1]

or a pharmaceutically acceptable salt, hydrate or solvate thereof, and (ii) a pharmaceutically acceptable carrier, wherein the pharmaceutically acceptable carrier comprises at least one species selected from the group consisting of a glycol, an oil, an alcohol, a flavoring agent, a preservative, a coloring agent, a starch, a sugar, microcrystalline cellulose, a granulating agent, a lubricant, a binder, a disintegrating agent, and a lipid, and wherein the composition is capable of inhibiting growth of fungi.

2. The pharmaceutical composition of claim 1, further comprising one or more further therapeutic ingredients.

3. The pharmaceutical composition of claim 1, formulated to be suitable for topical, oral, subcutaneous, intradermal, intramuscular, intravenous, intratumoral, intraarticular, rectal, dermal, buccal, sublingual, or intraocular administration.

4. A method of inhibiting the growth of fungi, said method comprising administering an effective amount of a pharmaceutical composition of claim 1 to an object or individual needing anti-fungal treatment.

5. The method of claim 4, wherein the pharmaceutical composition further comprises one or more further therapeutic ingredients.

6. The method of claim 4, wherein the pharmaceutical composition is formulated to be suitable for topical, oral, subcutaneous, intradermal, intramuscular, intravenous, intratumoral, intraarticular, rectal, dermal, buccal, sublingual, or intraocular administration.

7. The method of claim 4, wherein the fungi is selected from the group consisting of *Candida albicans* and *Cryptococcus neoformans*.

* * * * *